US007818052B2

(12) United States Patent
Litvak et al.

(10) Patent No.: US 7,818,052 B2
(45) Date of Patent: Oct. 19, 2010

(54) METHODS AND SYSTEMS FOR AUTOMATICALLY IDENTIFYING WHETHER A NEURAL RECORDING SIGNAL INCLUDES A NEURAL RESPONSE SIGNAL

(75) Inventors: Leonid M. Litvak, Los Angeles, CA (US); Edward H. Overstreet, Valencia, CA (US)

(73) Assignee: Advanced Bionics, LLC, Valencia, CA (US)

( * ) Notice: Subject to any disclaimer, the term of this patent is extended or adjusted under 35 U.S.C. 154(b) by 1540 days.

(21) Appl. No.: 11/142,152

(22) Filed: Jun. 1, 2005

(65) Prior Publication Data

US 2006/0287609 A1    Dec. 21, 2006

(51) Int. Cl.
*A61B 5/04*    (2006.01)
(52) U.S. Cl. .............................. 600/544; 600/545
(58) Field of Classification Search .................. 600/544, 600/545, 559; 607/2, 56, 117
See application file for complete search history.

(56) References Cited

U.S. PATENT DOCUMENTS

| | | | |
|---|---|---|---|
| 4,819,647 A | 4/1989 | Byers et al. | |
| 5,193,539 A | 3/1993 | Schulman et al. | |
| 5,193,540 A | 3/1993 | Schulman et al. | |
| 5,312,439 A | 5/1994 | Loeb | |
| 5,501,703 A | 3/1996 | Holsheimer et al. | |
| 5,938,688 A | 8/1999 | Schiff | |
| 6,016,449 A | 1/2000 | Fischell et al. | |
| 6,055,456 A | 4/2000 | Gerber | |
| 6,129,753 A | 10/2000 | Kuzma | |
| 6,164,284 A | 12/2000 | Schulman et al. | |
| 6,185,452 B1 | 2/2001 | Schulman et al. | |
| 6,208,894 B1 | 3/2001 | Schulman et al. | |
| 6,219,580 B1 | 4/2001 | Faltys et al. | |
| 6,272,382 B1 | 8/2001 | Faltys et al. | |
| 6,308,101 B1 | 10/2001 | Faltys et al. | |
| 6,381,496 B1 | 4/2002 | Meadows et al. | |
| 6,487,446 B1 | 11/2002 | Hill et al. | |
| 6,516,227 B1 | 2/2003 | Meadows et al. | |
| 6,539,263 B1 | 3/2003 | Schiff et al. | |
| 6,658,396 B1 * | 12/2003 | Tang et al. | ..................... 706/17 |
| 6,760,626 B1 | 7/2004 | Boveja | |
| 2001/0049480 A1 * | 12/2001 | John et al. | .................. 600/559 |
| 2003/0185408 A1 | 10/2003 | Causevic et al. | |
| 2005/0283090 A1 * | 12/2005 | Wells | .......................... 600/544 |

OTHER PUBLICATIONS

Spiegel et al., "Schaum's Outline of Theory and Problems of Statistics: Theory and Problems of Statistics", 3rd Ed, McGraw-Hill Professional, 1999, p. 202.*

* cited by examiner

*Primary Examiner*—Patricia C Mallari
*Assistant Examiner*—Christian Jang
(74) *Attorney, Agent, or Firm*—AdvantEdge Law Group, LLC

(57) ABSTRACT

Methods of automatically identifying whether a neural recording signal includes a neural response signal include fitting an artifact model to a neural recording signal to produce a fitted artifact model signal, determining a strength-of-response metric that describes a distance of the neural recording signal from the fitted artifact model signal, and identifying the neural recording signal as including a neural response signal if the strength-of-response metric is above a pre-determined threshold. Corresponding systems are also described.

20 Claims, 16 Drawing Sheets

METHODS AND SYSTEMS FOR AUTOMATICALLY IDENTIFYING WHETHER A NEURAL RECORDING SIGNAL INCLUDES A NEURAL RESPONSE SIGNAL

BACKGROUND

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that acoustic signals reach the cochlea and the hair cells. Some types of conductive hearing loss may also be treated by surgical procedures.

Sensorineural hearing loss, on the other hand, is due to the absence or the destruction of the hair cells in the cochlea which are needed to transduce acoustic signals into auditory nerve impulses. Thus, people who suffer from sensorineural hearing loss are unable to derive any benefit from conventional hearing aid systems.

To overcome sensorineural hearing loss, numerous cochlear implant systems—or cochlear prosthesis—have been developed. These devices seek to bypass the hair cells in the cochlea by presenting electrical stimulation directly to the auditory nerve fibers. This leads to the perception of sound in the brain and at least partial restoration of hearing function. To facilitate direct stimulation of the auditory nerve fibers, an array of electrodes may be implanted in the cochlea. A sound processor processes an incoming sound and translates it into electrical stimulation pulses applied by these electrodes which directly stimulate the auditory nerve.

Many cochlear implant systems, as well as other types of neural stimulators, are configured to measure the effectiveness of an electrical stimulation current applied to neural tissue (e.g., the auditory nerve) by using a process known as neural response imaging (NRI). In NRI, the neural stimulator delivers a stimulus to the neural tissue with a stimulating electrode and then records the resulting electrical activity of the neural tissue with a recording electrode. This resulting electrical activity is often referred to as an evoked neural response and occurs when the neural tissue depolarizes in response to the applied stimulus.

An evoked neural response may serve as a diagnostic measure to determine whether the neural stimulator is functioning correctly. NRI may also be used to determine optimal stimulation parameters for each electrode or electrode configuration. For example, NRI may be used to determine the lowest level of stimulating current that is required to evoke a neural response in a particular nerve. This information may then be used to optimize the stimulation parameters or settings of the cochlear implant system. NRI may also be used for a number of additional reasons.

In practice, however, the signal recorded by the recording electrode often includes undesirable signals that interfere with detection of the desired neural response. The terms "neural recording" and "neural recording signal" will be used herein and in the appended claims, unless otherwise specifically denoted, to refer to any signal recorded by the recording electrode. As will be explained in more detail below, a neural recording signal may include any combination of a neural response signal, noise, and/or stimulus artifact. Neural recording signals are sometimes referred to as evoked potential recordings.

As mentioned, a neural recording signal may include noise. Noise refers to any signal that is not correlated with the stimulus that is applied to the neural tissue by the neural stimulator. Noise is generally unpredictable.

Furthermore, a neural recording signal may also include stimulus artifact. Stimulus artifact includes signals, other than the neural response, that are correlated with the stimulus that is used to evoke the neural response. For example, the stimulus artifact may include the voltage potential of the stimulus pulse itself. Another source of stimulus artifact is cross-talk between the recording circuit and the stimulation circuit.

The presence of noise and stimulus artifact often makes it difficult to determine whether a neural recording includes a neural response. A number of conventional techniques exist for removing noise and any stimulus artifact from a signal. However, these techniques are often ineffective when applied to a neural recording signal.

For example, filtering may be used to remove noise that has a different frequency than the frequency of a particular signal of interest. However, in neural stimulation systems, the frequency of the noise and the frequency of an evoked neural response are often similar. Thus, conventional filtering cannot always be used to remove noise from a neural recording.

Signal correlation may also be used to remove noise from a signal of interest. In signal correlation, a measured signal is correlated with a known reference signal to remove uncorrelated noise from the measured signal. However, evoked neural responses are often variable from patient to patient. Hence, a single reference signal cannot be used to correlate evoked neural responses from multiple patients. The signal correlation technique is therefore ineffective in many instances in removing noise from a neural recording.

Likewise, a number of conventional techniques exist for removing stimulus artifact from a neural recording. These techniques include alternating polarity, forward masking, third-phase compensation, and scaled template techniques. For example, in the alternating polarity technique, the neural response within the neural recording is estimated to be the average of the responses to a first stimulation pulse having a first polarity (e.g. cathodic) and a second stimulation pulse having the opposite polarity (e.g. anodic). The neural response stays the same polarity with the reverse in polarity of the stimulus. However, the stimulus artifact reverses polarity with the reverse in polarity of the stimulus. Consequently, the average response to the two polarities has a lower artifact component than either of the responses taken by themselves. While the alternating polarity technique is sometimes successful in reducing stimulus artifact in a neural recording, it does not eliminate it in all cases. Furthermore, the alternating polarity, as well as the other conventional techniques, often leaves large, residual stimulus artifacts in the neural recording.

SUMMARY

Methods of automatically identifying whether a neural recording signal includes a neural response signal include fitting an artifact model to a neural recording signal to produce a fitted artifact model signal, determining a strength-of-response (SOR) metric that describes a distance of the neural recording signal from the fitted artifact model signal, and identifying the neural recording signal as including a neural response signal if the strength-of-response metric is above a pre-determined threshold.

Systems for automatically identifying whether a neural recording signal includes a neural response signal include one or more devices configured to fit an artifact model to a neural recording signal to produce a fitted artifact model signal, determine a strength-of-response (SOR) metric that describes a distance of the neural recording signal from the fitted artifact model signal, and automatically identify the neural recording signal as including a neural response signal if said strength-of-response metric is above a pre-determined threshold.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Methods and systems for automatically identifying a neural recording signal as including a neural response signal are described herein. An artifact model is fitted to a neural recording signal to produce a fitted artifact model signal. A strength-of-response (SOR) metric that describes a distance of the neural recording signal from the fitted artifact model signal may then be computed. The neural recording signal may be identified as including a neural response signal if the strength-of-response metric is above a pre-determined threshold. Conversely, the neural recording signal may be identified as only including noise and stimulus artifact signals if the strength-of-response metric is below the pre-determined threshold.

Systems for automatically identifying a neural recording signal as including a neural response signal include one or more devices configured to fit an artifact model to a neural recording signal to produce a fitted artifact model signal, determine a strength-of-response (SOR) metric that describes a distance of the neural recording signal from the fitted artifact model signal, and automatically identify the neural recording signal as including a neural response signal if said strength-of-response metric is above a pre-determined threshold.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
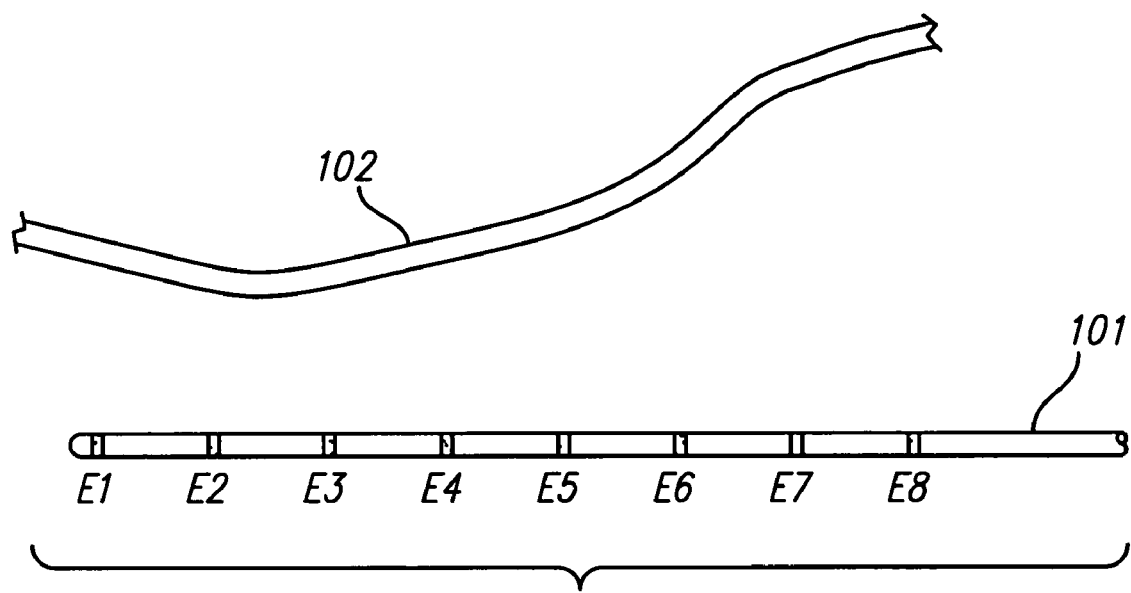
FIG. 1 shows a lead having an electrode array with electrodes E1 through E8 according to principles described herein.

FIG. 1 shows a lead (101) supporting an electrode array with electrodes E1 through E8. The lead (101) may be attached to a neural stimulator (not shown). The stimulator is configured to provide an electrical current via the electrode array to stimulate target tissue, e.g., neural tissue (102). The stimulation current output at each of the electrodes (E1-E8) may be independently controlled by the stimulator. The lead (101) of FIG. 1 includes eight electrodes for illustrative purposes only. It will be recognized that the lead (101) may include any number of electrodes. Furthermore, the electrodes may be arranged in any of a number of configurations. For example, the electrodes may be arranged as an array having at least two or at least four collinear electrodes. In some embodiments, the electrodes are inductively coupled to the stimulator. The lead (101) may be thin (e.g., less than 3 millimeters in diameter) and flexible such that the lead (101) may be readily positioned near target neural tissue (102). Alternatively, the electrodes may be coupled directly to a leadless stimulator.

In some embodiments, each electrode (E1-E8) may be selectively configured to function as a stimulating electrode or a recording electrode as best serves a particular application. For example, E1 may be a used as a stimulating electrode and E2 may be used as a recording electrode. A stimulus, e.g., an electrical stimulation current, may then be applied to the neural tissue (102) via the stimulating electrode E1. The resulting electrical activity of the nerve (102) when the nerve (102) depolarizes in response to the applied stimulus is recorded with the recording electrode E2. As mentioned previously, this electrical activity is referred to as an evoked neural response or simply a neural response.

Figure 2:
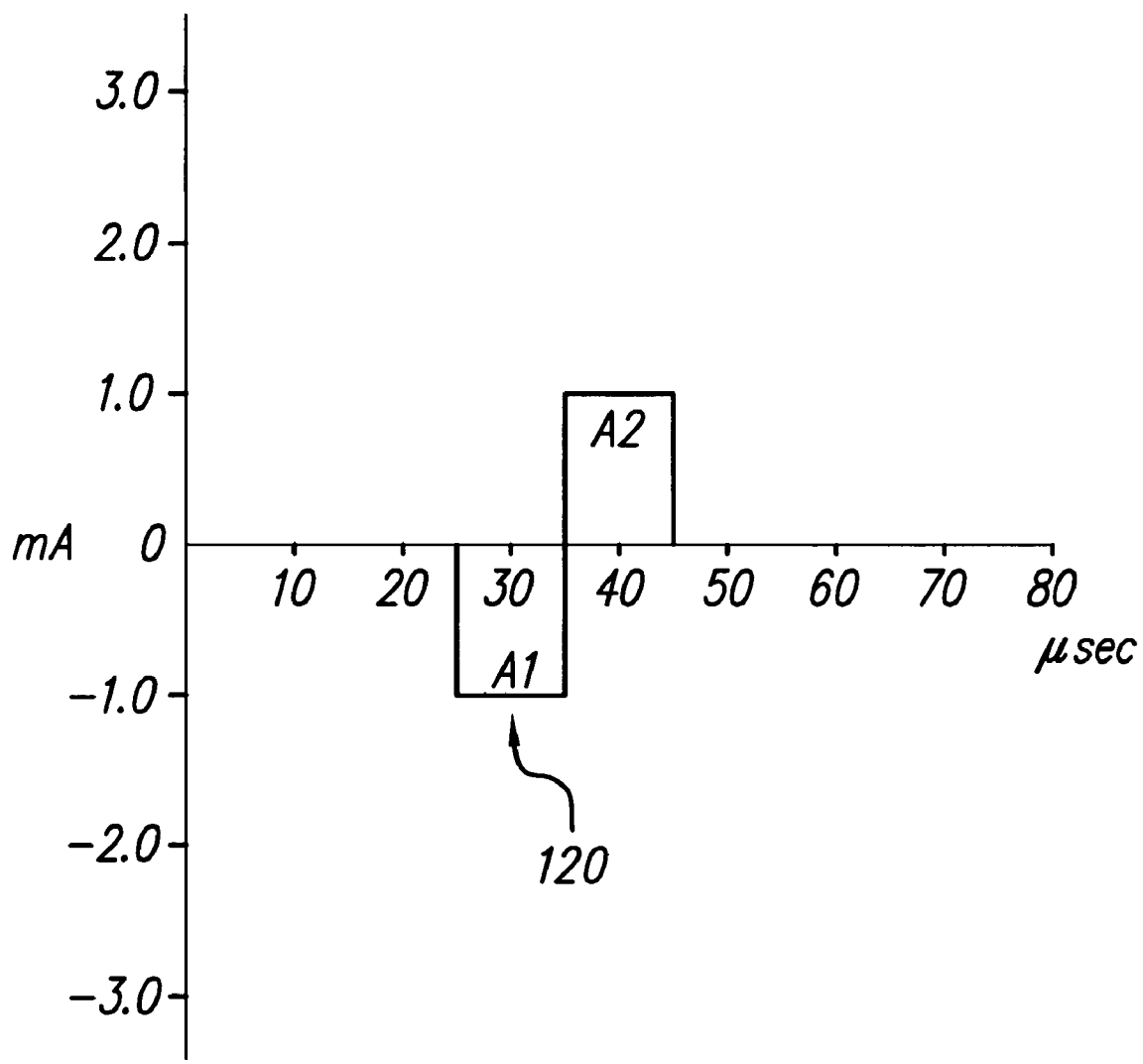
FIG. 2 illustrates an exemplary stimulus that may be delivered to neural tissue via a stimulating electrode according to principles described herein.

FIG. 2 illustrates an exemplary stimulus (120), e.g., an electrical stimulation current pulse, that may be delivered to neural tissue via a stimulating electrode. The stimulus (120) of FIG. 2 is biphasic. In other words, the stimulus (120) includes two parts—a negative first phase having an area A1 and a positive second phase having an area A2. It is usually the negative phase that causes neural tissue to depolarize (fire). The biphasic stimulus (120) shown in FIG. 2 has an amplitude of 1 milliamp (ma) and a pulse width of 20 microseconds (μsec) for illustrative purposes only. It will be recognized that any of the characteristics of the stimulus (120), including, but not limited to, the pulse shape, amplitude, pulse width, frequency, burst pattern (e.g., burst on time and burst off time), duty cycle or burst repeat interval, ramp on time, and ramp off time may vary as best serves a particular application.

The biphasic stimulus (120) shown in FIG. 2 is "charge balanced" because the negative area A1 is equal to the positive area A2. A charge-balanced biphasic pulse is often employed as the stimulus to minimize electrode corrosion and charge build-up which can harm surrounding tissue. However, it will be recognized that the biphasic stimulus (120) may alternatively be charge-imbalanced as best serves a particular application.

In some embodiments, when the amplitude and pulse width of the stimulus (120) of FIG. 2 reach a supra-threshold (i.e., a threshold stimulus large enough to depolarize a target nerve), the voltage gradient at some surface point on the nerve (102; FIG. 1) will be sufficiently negative as to cause the nerve (102; FIG. 1) to depolarize from its resting state and propagate an electrical signal along the length of the nerve (102). The voltage gradient of this electrical signal propagation can be captured with a recording electrode as the evoked neural response of the target nerve.

Before discussing the present methods and systems of identifying a neural recording signal that includes a neural response signal, it is helpful to understand the components of a number of exemplary neural stimulators in which the present methods and systems may be employed.

Figure 3:
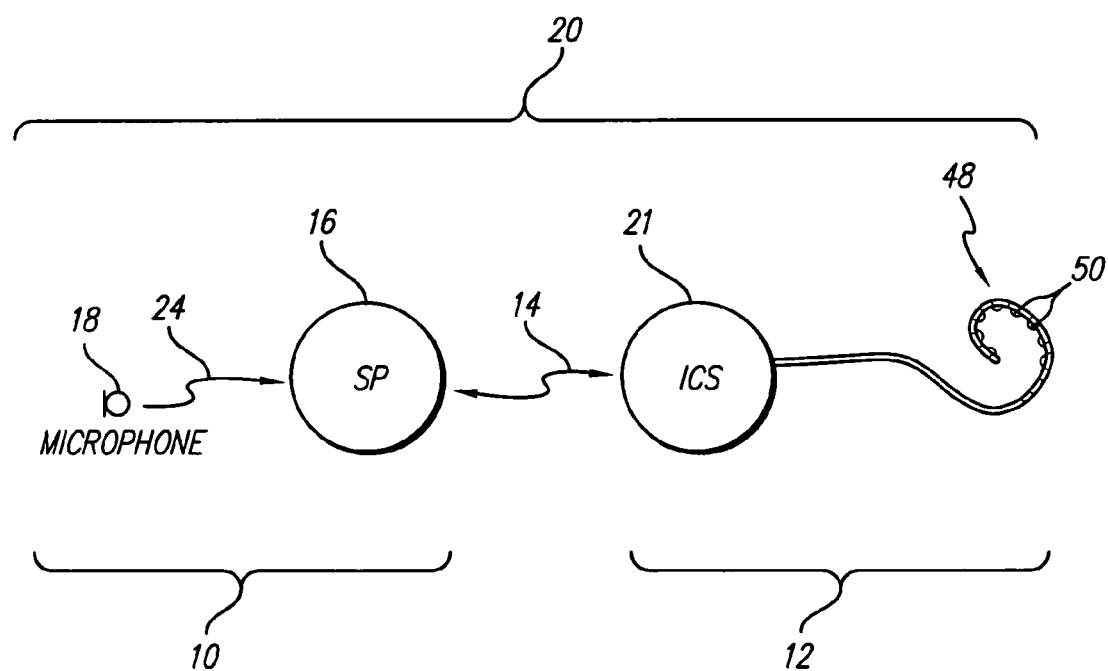
FIG. 3 shows an exemplary cochlear implant system that may be used as a neural stimulator according to principles described herein.

FIG. 3 shows an exemplary cochlear implant system (20) that may be used as a neural stimulator in accordance with the present methods and systems. Exemplary cochlear implant systems suitable for use as described herein include, but are not limited to, those disclosed in U.S. Pat. Nos. 6,219,580; 6,272,382; and 6,308,101, all of which are incorporated herein by reference in their respective entireties. The cochlear implant system (20) includes a speech processor portion (10) and a cochlear stimulation portion (12). The speech processor portion (10) may include a speech processor (SP) (16), a microphone (18), and/or additional circuitry as best serves a particular application. The cochlear stimulation portion (12) may include an implantable cochlear stimulator (ICS) (21), a number of electrodes (50) arranged in an electrode array (48), and/or additional circuitry as best serves a particular application. The components within the speech processor portion (10) and the cochlear stimulation portion (12) will be described in more detail below.

The microphone (18) of FIG. 3 is configured to sense acoustic signals and convert such sensed signals to corresponding electrical signals. The electrical signals are sent to the SP (16) over an electrical or other suitable link (24). Alternatively, the microphone (18) may be connected directly to, or integrated with, the SP (16). The SP (16) processes these converted acoustic signals in accordance with a selected speech processing strategy to generate appropriate control signals for controlling the ICS (21). These control signals may specify or define the polarity, magnitude, location (i.e., which electrode pair or electrode group receive the stimulation current), and timing (i.e., when the stimulation current is to be applied to a particular electrode pair) of the stimulation current that is generated by the ICS (21).

The electrode array (48) of FIG. 3 is adapted to be inserted within a duct of the cochlea. As shown in FIG. 3, the array (48) includes a multiplicity of electrodes (50), e.g., sixteen electrodes, spaced along its length. Each of the electrodes (50) is individually connected to the ICS (21). The electrode array (48) may be substantially as shown and described in U.S. Pat. No. 4,819,647 or U.S. Pat. No. 6,129,753, each of which is incorporated herein by reference in its respective entirety. Electronic circuitry within the ICS (21) is configured to apply stimulation current to selected pairs or groups of the individual electrodes (50) included within the electrode array (48) in accordance with a specified stimulation pattern defined by the SP (16).

The ICS (21) and the SP (16) may be electronically connected via a suitable data or communications link (14). In some embodiments, the SP (16) and the microphone (18) comprise an external portion of the cochlear implant system (20) and the ICS (21) and the electrode array (48) comprise an implantable portion of the system (20). In alternative embodiments, one or more portions of the SP (16) are included within the implantable portion of the cochlear implant system (20). The implantable portion of the cochlear implant system (20) is implanted within the patient's body. Thus, the data link (14) is a transcutaneous (through the skin) data link that allows power and control signals to be sent from the SP (16) to the ICS (21). In some embodiments, data and status signals may also be sent from the ICS (21) to the SP (16).

The external and implantable portions of the cochlear implant system (20) may each include one or more coils configured to transmit and receive power and/or control signals via the data link (14). For example, the external portion of the cochlear implant system (20) may include an external coil (not shown) and the implantable portion of the cochlear implant system (20) may include an implantable coil (not shown). The external coil and the implantable coil may be inductively coupled to each other, thereby allowing data to be transmitted between the external portion and the implantable portion. The data may include, for example, the magnitude and polarity of a sensed acoustic signal. The external coil may also transmit power from the external portion to the implantable portion of the cochlear implant system (20). It will be noted that, in some embodiments, both the SP (16) and the ICS (21) may be implanted within the patient, either in the same housing or in separate housings. If the SP (16) and the ICS (21) are in the same housing, the link (14) may be realized with a direct wire connection within such housing. If the SP (16) and the ICS (21) are in separate housings, the link (14) may be an inductive link, for example.

Figure 4:
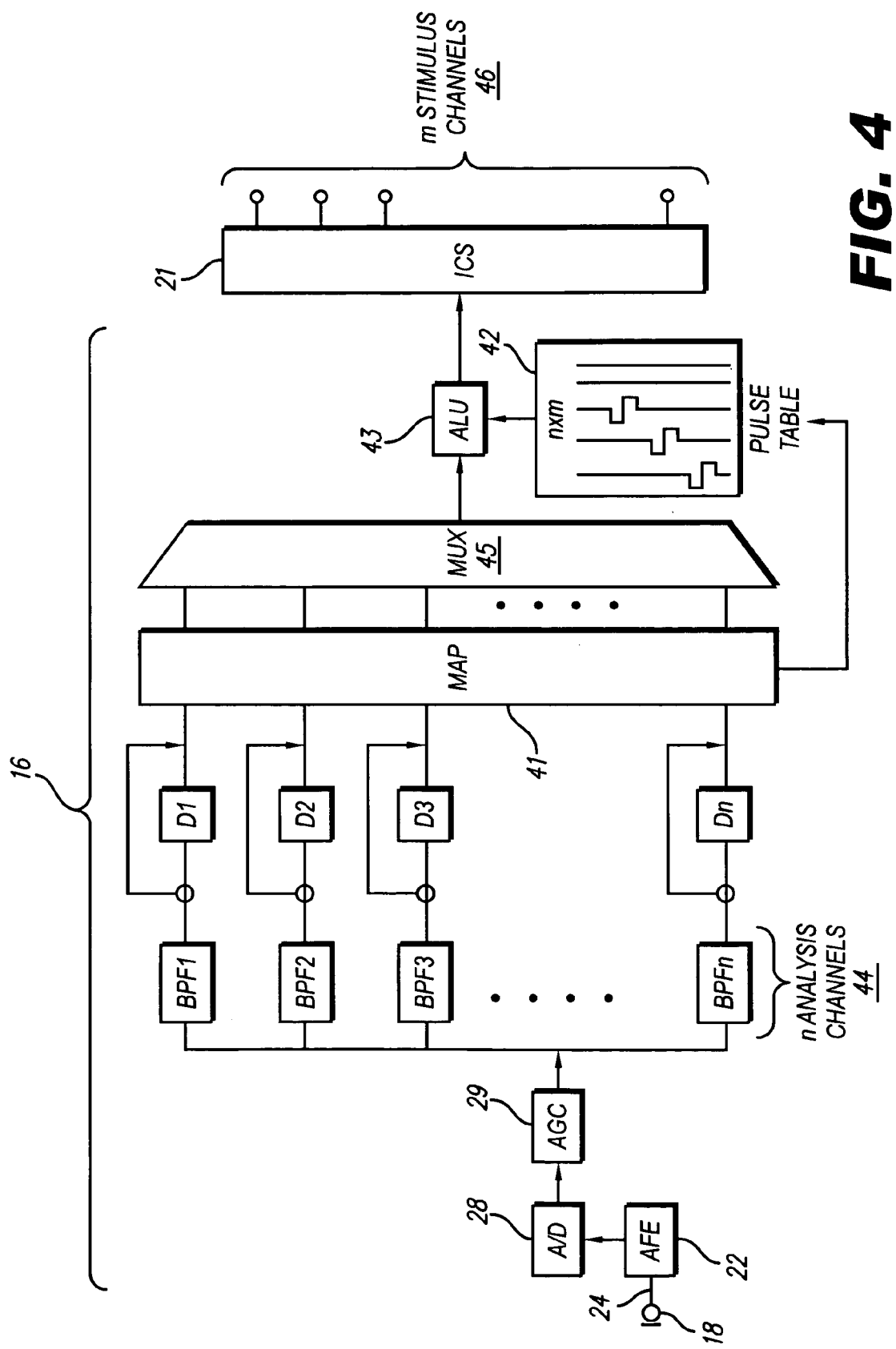
FIG. 4 is a functional block diagram of an exemplary speech processor and an implantable cochlear stimulator according to principles described herein.

FIG. 4 is a functional block diagram of an exemplary SP (16) and ICS (21). The functions shown in FIG. 4 are merely representative of the many different functions that may be performed by the SP (16) and/or the ICS (21). A more complete description of the functional block diagram of the SP (16) and the ICS (21) is found in U.S. Pat. No. 6,219,580, which is incorporated herein by reference in its entirety.

As shown in FIG. 4, the microphone (18) senses acoustic information, such as speech and music, and converts the acoustic information into one or more electrical signals. These signals are then amplified in audio front-end (AFE) circuitry (22). The amplified audio signal is then converted to a digital signal by an analog-to-digital (A/D) converter (28). The resulting digital signal is then subjected to automatic gain control using a suitable automatic gain control (AGC) function (29).

After appropriate automatic gain control, the digital signal is then processed in one of a number of digital signal processing or analysis channels (44). For example, the SP (16) may include, but is not limited to, eight analysis channels (44). Each analysis channel (44) may respond to a different frequency content of the sensed acoustical signal. In other words, each analysis channel (44) includes a band-pass filter (BP1-BPFn) or other type of filter such that the digital signal is divided into n frequency channels. The lowest frequency filter may be a low-pass filter, and the highest frequency filter may be a high-pass filter.

As shown in FIG. 4, each analysis channel (44) may also include a detection stage (D1-Dn). Each detection stage (D1-Dn) may include an energy detection circuit (not shown), which may be realized, e.g., through a rectification circuit followed by an integrator circuit. As shown in FIG. 4, each of the detection stages (D1-Dn) may alternatively be bypassed depending on the particular signal processing strategy being used.

After energy detection, or bypassing of such, the signal from each of the n analysis channels (44) is forwarded to a mapping stage (41). The mapping stage (41) may be configured to map the signals in each of the analysis channels (44) to one or more of the m stimulus channels (46). The mapping stage (41) may be further configured to perform additional processing of the signal, such as signal compression. The signals output by each analysis channel (44) may then be serialized by a multiplexer (45) into one serial data channel. The multiplexed signal may then be further processed according to information included in a pulse table (42) connected to an arithmetic logic unit (ALU) (43). After the signal is appropriately processed, compressed, and mapped, the signal may be input into the ICS (21) to control the actual stimulus patterns that are applied to the patient via the electrode array (48; FIG. 3).

As mentioned, each of the n analysis channels (44) may be mapped to one or more stimulus channels (46). In other words, the information contained in the n analysis channels (44) controls the stimulus patterns that are applied to the patient by the ICS (21) and its associated electrode array (48; FIG. 3). Stimulus current may be applied to any number of stimulation sites within the patient's cochlea via the m stimulus channels (46). As used herein and in the appended claims, the term "stimulation site" will be used to refer to a target area or location at which the stimulus current is applied. For example, a stimulation site may refer to a particular location in the neural tissue of a cochlear implant patient. Through appropriate weighting and sharing of currents between the electrodes (50; FIG. 3), stimulus current may be applied to any stimulation site along the length of the electrode array (48; FIG. 3).

Figures 5A, 5B:
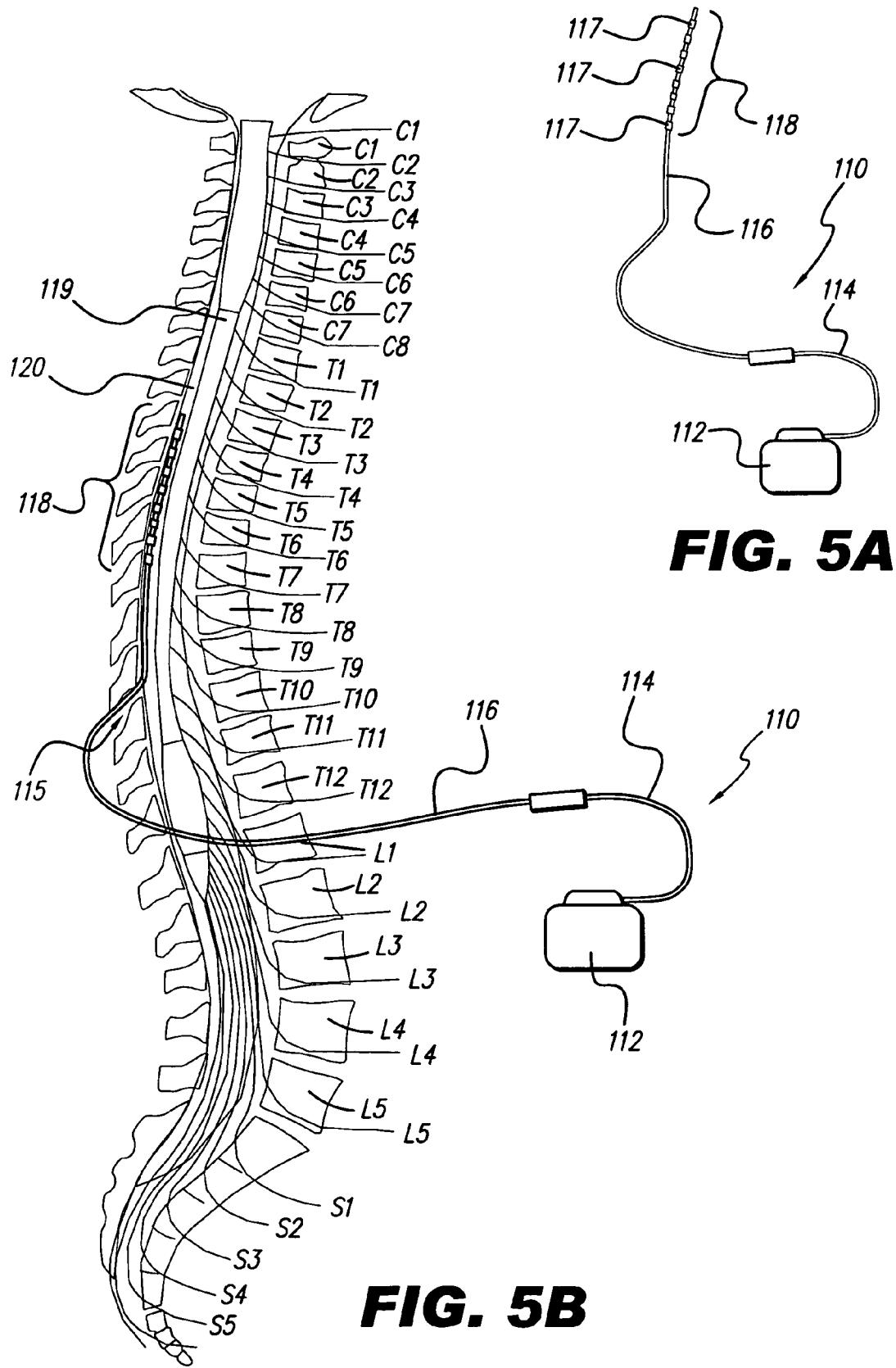
FIGS. 5A and 5B show a spinal cord stimulator (SCS) system that may be used as a neural stimulator according to principles described herein.

FIGS. 5A and 5B show a spinal cord stimulator (SCS) system (110) that may be used as a neural stimulator in accordance with the present methods and systems. The SCS (110) may be used to treat a number of different medical conditions such as, but not limited to, chronic pain.

As shown in FIG. 5A, the SCS (110) may include an implantable pulse generator (IPG) (112), a lead extension (114), and an electrode lead (116) having an electrode array (118) thereon. The electrode array (118) includes a plurality of electrodes (117). The electrodes (117) may be arranged, as shown in FIG. 5A, in an in-line array near the distal end of the lead (116). Other electrode array configurations may also be used. The lead extension (114) need not always be used with the SCS (110), but may be used depending on the physical distance between the IPG (112) and the stimulation site within the patient. The IPG (112) is configured to generate stimulation current pulses that are applied to a stimulation site via one or more of the electrodes (117). Exemplary spinal cord stimulators suitable for use as described herein include, but are not limited to, those disclosed in U.S. Pat. Nos. 5,501,703; 6,487,446; and 6,516,227, all of which are incorporated herein by reference in their respective entireties.

FIG. 5B shows that the electrode array (118) of the SCS (110) may be implanted in the epidural space (120) of a patient in close proximity to the spinal cord (119). Because of the lack of space near the lead exit point (115) where the electrode lead (116) exits the spinal column, the IPG (112) is generally implanted in the abdomen or above the buttocks. However, it will be recognized that the IPG (112) may be implanted in any suitable implantation site. The lead extension (114) facilitates implanting the IPG (112) at a location that is relatively distant from the lead exit point (115).

The cochlear implant system (20; FIG. 3) and the SCS (110; FIG. 5A) are merely illustrative of many types of neural stimulators that may be used to perform NRI. For example, the neural stimulator may additionally or alternatively include an implantable pulse generator (IPG) coupled to one or more leads having a number of electrodes, a deep brain stimulator, an implantable microstimulator, an external stimulator, or any other type of stimulator configured to perform NRI. Exemplary IPGs suitable for use as described herein include, but are not limited to, those disclosed in U.S. Pat. Nos. 6,381,496, 6,553,263; and 6,760,626. Exemplary deep brain stimulators suitable for use as described herein include, but are not limited to, those disclosed in U.S. Pat. Nos. 5,938,688; 6,016,449; and 6,539,263. Exemplary implantable microstimulators, such as the BION® microstimulator (Advanced Bionics® Corporation, Valencia, Calif.), suitable for use as described herein include, but are not limited to, those disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

As mentioned, it is often desirable to deliver a stimulus to neural tissue with a stimulating electrode and then record the resulting electrical activity of the neural tissue with a recording electrode. This resulting electrical activity is referred to as an evoked neural response or simply, a neural response, and occurs when the neural tissue depolarizes in response to the applied stimulus.

For example, in a normal ear, a single auditory nerve fiber or cell generates an action potential when the cell's membrane is depolarized to a threshold value, after which a spike occurs. Sodium ions entering the cell make the inside of the cell more positive, that is, depolarized. In some embodiments, an electrical stimulation current may be used to depolarize the nerve cell. This depolarization effect can be likened to taking a photograph by pressing the shutter button on a camera. Pressing on the button has no effect until it crosses a threshold pressure, and then "click"—the shutter opens and the film is exposed. In the same way, depolarizing a neuron has no effect until the depolarization reaches a threshold, and then, all at once, an action potential is generated.

Figure 6C:
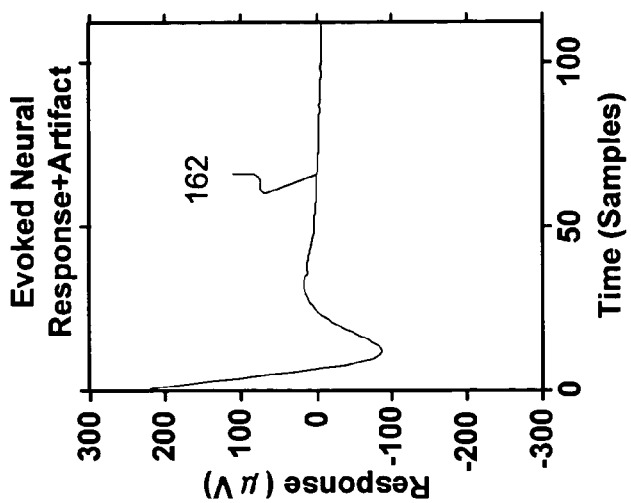
FIG. 6C is a graph depicting an exemplary neural recording signal according to principles described herein.

The evoked neural response as recorded by the recording electrode includes a sum of action potentials of a number of nerve cells. FIG. 6A is a graph depicting an exemplary evoked neural response signal (160). As shown in FIG. 6A, the horizontal axis represents time in samples and the vertical axis represents the amplitude of the response in microvolts (µV). As shown in FIG. 6A, the evoked neural response signal (160) is typically characterized by a first negative peak (N1) followed by a first positive peak (P1). It will be recognized that evoked neural responses differ in timing and amplitude from patient to patient.

Unfortunately, the recording electrode may additionally or alternatively record noise and/or stimulus artifact. In general, a neural recording may include any combination of a neural response signal, noise, and/or stimulus artifact. In some instances, the neural recording obtained by the recording electrode only includes stimulus artifact and noise. For example, if the stimulus pulse is too low to trigger depolarization of the nerve (102), the nerve (102) will not produce a neural response and the recording electrode will only record the stimulus artifact and any noise that is present.

Figure 6B:
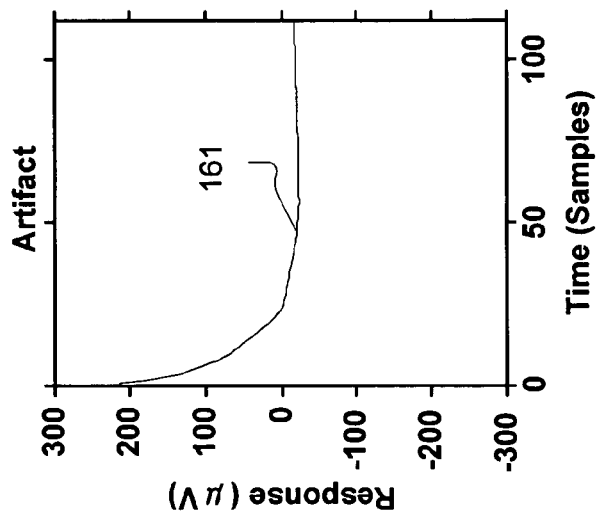
FIG. 6B is a graph depicting an exemplary artifact signal according to principles described herein.
Figure 6A:
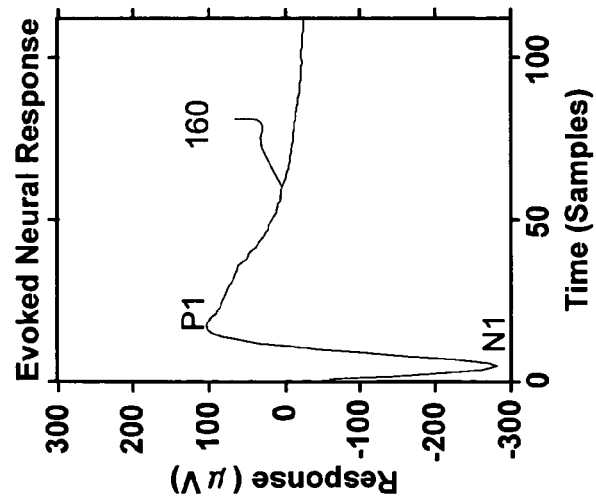
FIG. 6A is a graph depicting an exemplary evoked neural response signal according to principles described herein.

FIG. 6B is a graph depicting an exemplary artifact signal (161). The artifact signal (161) is typically characterized as a sum of two decaying exponentials, one with a fast time constant and one with a slow time constant.

FIG. 6C is a graph depicting a neural recording signal (162) that includes both the evoked neural response signal (160) of FIG. 6A and the artifact signal (161) of FIG. 6B. As shown in FIG. 6C, the neural recording signal (162) is a sum of the evoked neural response signal (160; FIG. 6A) and the artifact signal (161; FIG. 6B).

Figure 7A:
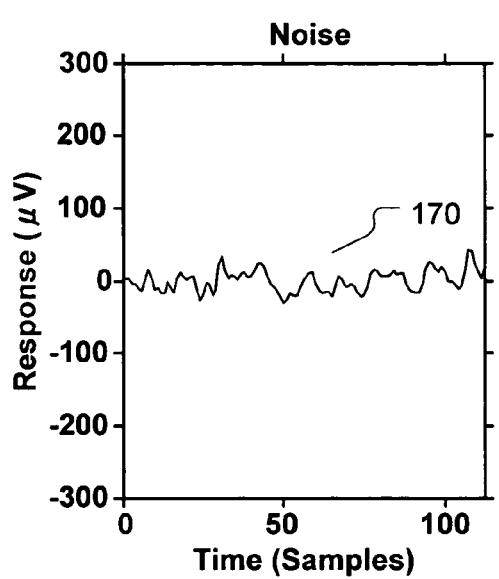
FIG. 7A is a graph depicting an exemplary noise signal according to principles described herein.

As mentioned previously, the neural recording signal obtained by a recording electrode may also include noise. Noise refers to any signal that is not correlated with the stimulus pulse and is generally unpredictable. FIG. 7A is a graph depicting an exemplary noise signal (170) that may be recorded by the recording electrode. Because the noise signal (170) is unpredictable, the noise signal (170) may have any frequency or amplitude.

Figure 7B:
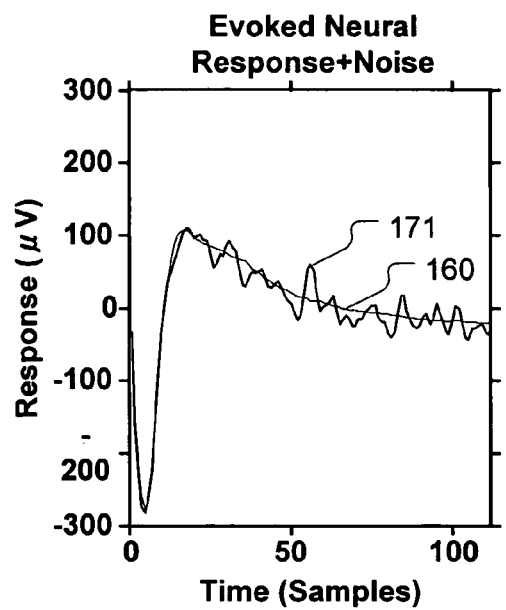
FIG. 7B is a graph depicting the effect of the noise signal of FIG. 7A on the evoked neural response signal of FIG. 6A according to principles described herein.
Figure 7C:
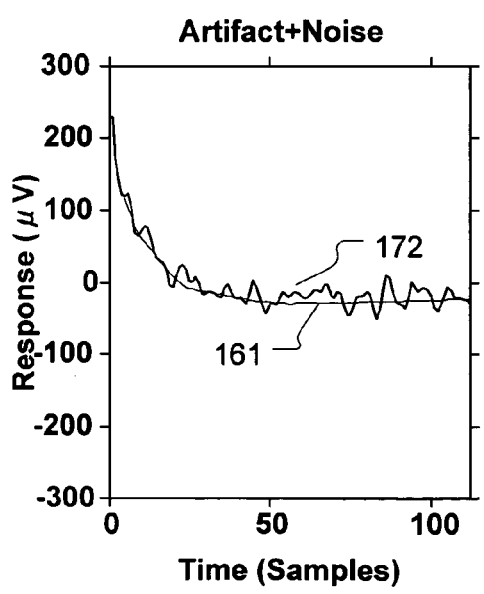
FIG. 7C is a graph depicting the effect of the noise signal of FIG. 7A on the artifact signal of FIG. 6B according to principles described herein.
Figure 7D:
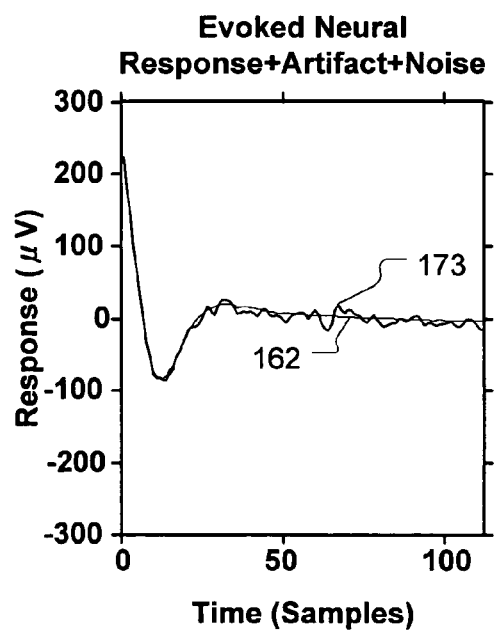
FIG. 7D is a graph depicting the effect of the noise signal of FIG. 7A on the neural recording signal of FIG. 6C according to principles described herein.

FIGS. 7B-7D are graphs depicting the effect (171) of the noise signal (170; FIG. 7A) on the evoked neural response signal (160) of FIG. 6A, the effect (172) of the noise signal (170; FIG. 7A) on the artifact signal (161) of FIG. 6B, and the effect (173) of the noise signal (170; FIG. 7A) on the neural recording signal (162) of FIG. 6C, respectively.

It is often desirable to determine whether a neural recording signal includes a neural response signal or whether the neural recording signal only includes noise and/or artifact signals. Currently, medical practitioners typically need to be trained to identify signals as containing valid neural responses from a visual display of the neural recording signal. For example, a typical neural response signal of the auditory nerve to a stimulus pulse includes a negative peak followed by a positive peak, such as the signal (160) shown in FIG. 6A. Waveforms that do not fall into this pattern are assumed to be recordings that contain only noise and/or stimulus artifact. However, because medical practitioners may have various degrees of training, the results of identifying signals containing valid neural responses may vary greatly from one practitioner to the next. In addition, some valid neural responses do not follow typical neural response patterns. Whether these responses will be correctly identified as valid neural responses depends on the judgment of the practitioner.

Figure 8:
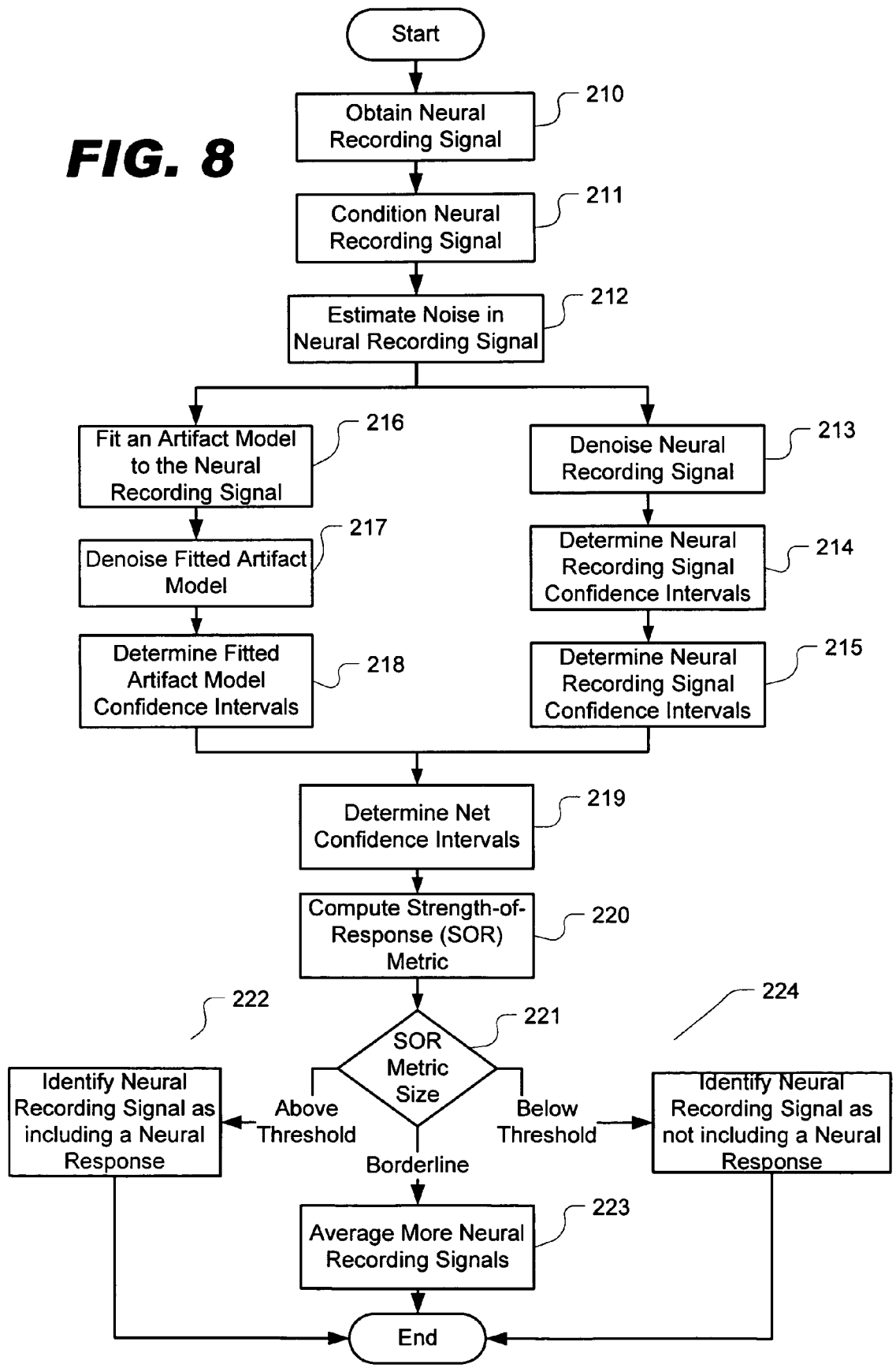
FIG. 8 is a flow chart illustrating an exemplary method of automatically identifying a neural recording signal that includes a neural response signal according to principles described herein.

To overcome the inaccuracies of practitioner identification of valid neural responses and to improve NRI performance, an exemplary method of automatically identifying a neural recording signal that includes a neural response signal will now be described. FIG. 8 is a flow chart illustrating an exemplary method of automatically identifying a neural recording signal that includes a neural response signal. The method may be used in connection with any type of neural stimulator. The steps shown in FIG. 8 and described below may be modified, reordered, removed, and/or added to as best serves a particular application. Furthermore, it will be recognized that a computer, digital signal processor (DSP), mathematical application, or any other suitable device, signal processor, software, firmware, or application may be used to implement one or more of the steps described in connection with FIG. 8.

As shown in FIG. 8, a neural recording signal is first obtained (step 210). As described above, the neural recording signal may be obtained by stimulating neural tissue with a stimulating electrode and then recording the electrical response of the neural tissue with a recording electrode. It will be recognized that the neural recording signal may be evoked in response to stimulus applied to any neural tissue by any neural stimulator. For example, the neural recording signal may capture a neural response evoked by a stimulus applied to the auditory nerve with a cochlear implant system.

Once the neural recording signal has been obtained (step 210), the neural recording signal is conditioned (step 211). In some embodiments, the neural recording signal is conditioned by removing the mean of the data within the neural recording, removing a trend from the data, and/or removing an overall DC voltage level from the data. The neural recording signal may additionally or alternatively be conditioned using any other suitable conditioning technique.

The noise that is present in the neural recording signal is then estimated (step 212). A number of different techniques may be used to estimate the nose in the neural recording signal. For example, the noise may be estimated by computing the standard deviation of the data near the tail of the neural recording signal. Alternatively, the noise may be directly estimated by analyzing variability between a number of different neural recording signals that are obtained.

The neural recording signal is then denoised (step 213). The neural recording signal may be denoised using any of a number of different techniques. For example, the neural recording signal may be denoised by applying principle component analysis, as is more fully described in a related application entitled "Methods and Systems for Denoising a Neural Recording Signal" to Litvak et al., 11/141,824, which application was filed simultaneously with the present application on Jun. 1, 2005. The 11/141,824 application is incorporated herein by reference in its entirety.

An exemplary method of denoising a neural recording signal by applying principal component analysis will now be described in connection with the flow chart shown in FIG. 9. The term "denoising" will be used herein and in the appended claims, unless otherwise specifically denoted, to refer to decreasing or removing noise from a neural recording signal or any other signal as best serves a particular application. The method may be used in connection with any type of neural stimulator. The steps shown in FIG. 9 and described below may be modified, reordered, removed, and/or added to as best serves a particular application.

Figure 9:
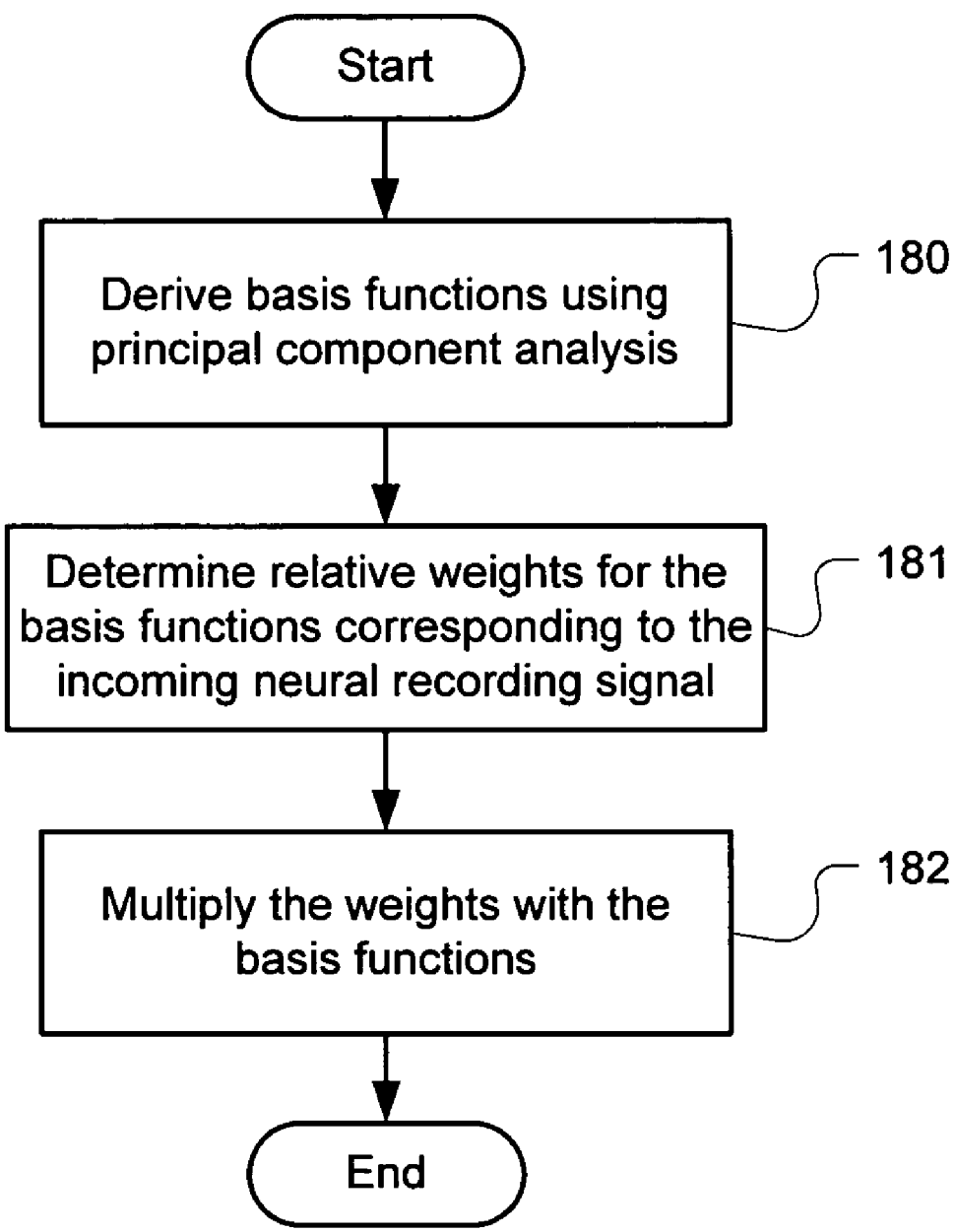
FIG. 9 is a flow chart illustrating an exemplary method of denoising a neural recording signal according to principles described herein.

As shown in FIG. 9, a number of basis functions are first derived using principal component analysis to describe a set of previously collected neural recording signals (step 180). Principal component analysis is a statistical technique used to derive a number of functions that, when summed together, describe a given set of data. These functions are often referred to as basis functions or principal components, both of which terms will be used interchangeably herein and in the appended claims unless otherwise specifically denoted.

An example of deriving a number of basis functions that describe a set of neural recording signals corresponding to the auditory nerve will now be given. It will be recognized that the following example is merely illustrative and that the neural recording signal may be evoked in response to stimulus applied to any neural tissue by any neural stimulator.

A large number of neural recording signals were evoked and recorded by audiologists over a period of time. Each measured waveform was computed by averaging the response to a cathodic-anodic and anodic-cathodic stimulus pulse. A two-point averaging filter was then applied to the data. In addition, synchronized noise was measured by recording the response to stimulation with zero current. The synchronized noise was then subtracted from the response to the cathodic-anodic and anodic-cathodic stimulus pulse.

The evoked neural recording signals were then collected into a measurement matrix $M=[m_1 \ldots m_{8000}]$. As used herein and in the appended claims, unless otherwise specifically denoted, bold capital letters will be used to refer to matrices and bold lower-case letters will be used to refer to vectors. Hence, M is a matrix containing 8,000 measured neural recording signals $m_1$ through $m_{8000}$. Although M contains 8,000 measured neural recording signals in the present example, it will be recognized that M may contain any number of measured neural recording signals as best serves a particular application.

Eigenvalue decomposition was then used to compute the principal components of M. MATLAB™ or any other mathematical tool may be used to perform the eigenvalue decomposition. First, the covariance matrix $C_M=COV(M')$ was computed. A vector of eigenvalues ($\lambda$) and a matrix of eigenvectors arranged in columns ($V_{full}$) were then computed. The matrix $V_{full}$ contains the full components that account entirely for the measurement matrix M.

Because the covariance matrix $C_M$ is symmetric, the eigenvectors within the matrix $V_{full}$ are orthogonal. The eigenvectors within the matrix $V_{full}$ may be normalized to have a norm of one.

Figure 10:
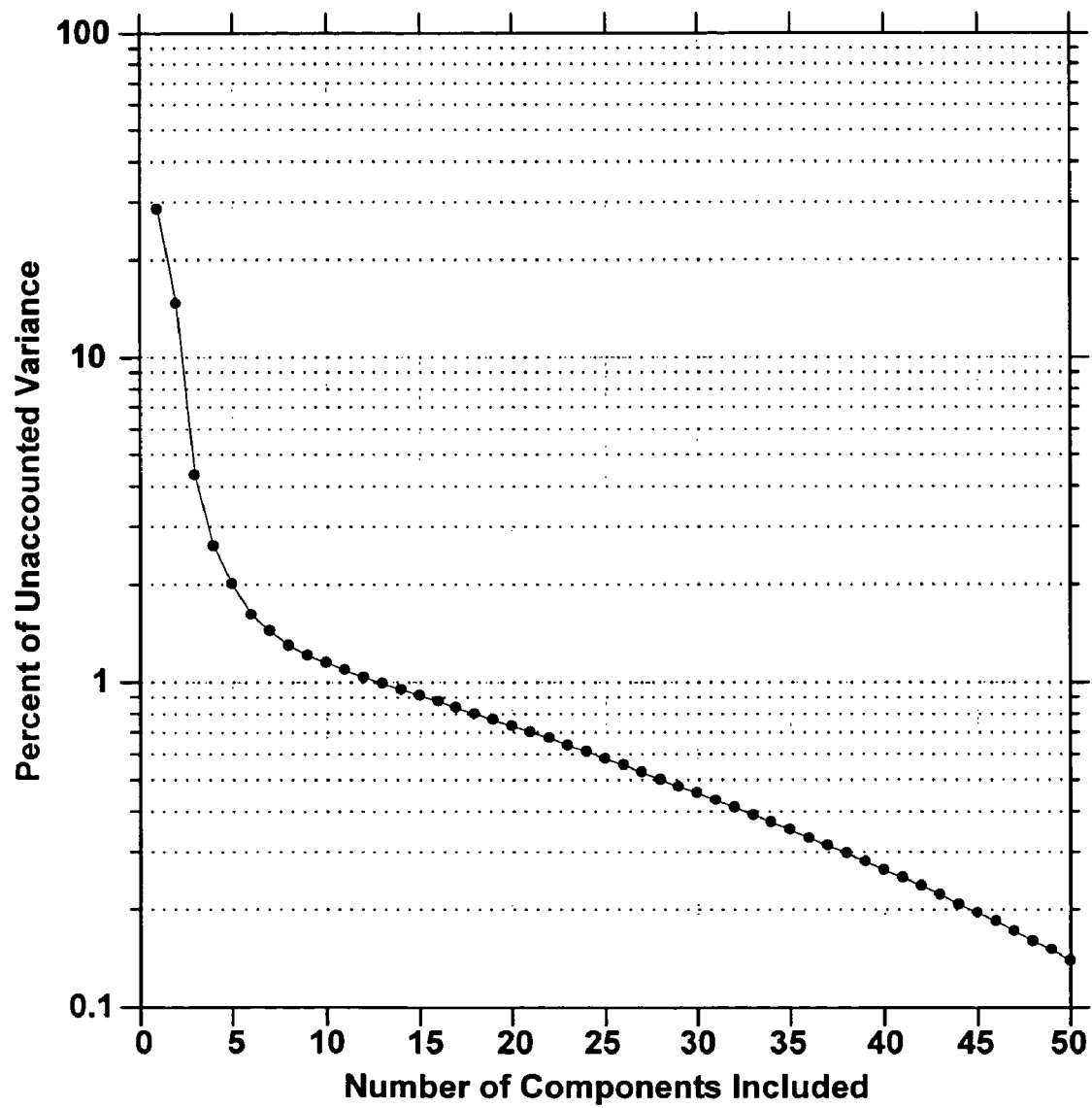
FIG. 10 is a graph showing the percent of unaccounted variance in a matrix of evoked neural recording signals as a function of number of components according to principles described herein.

Although $V_{full}$ contains the full components that account entirely for the data contained in measurement matrix M, it can be shown that a lesser number of these components may sufficiently account for the data in M. FIG. 10 is a graph showing the percent of unaccounted variance in M as a function of the number of components. As shown in FIG. 10, the percent of unaccounted variance decreases as more components are included. However, as shown in FIG. 10, a small number of components (e.g., 5 to 10 components) may account for approximately 98 to 99 percent of the variance.

Figure 11:
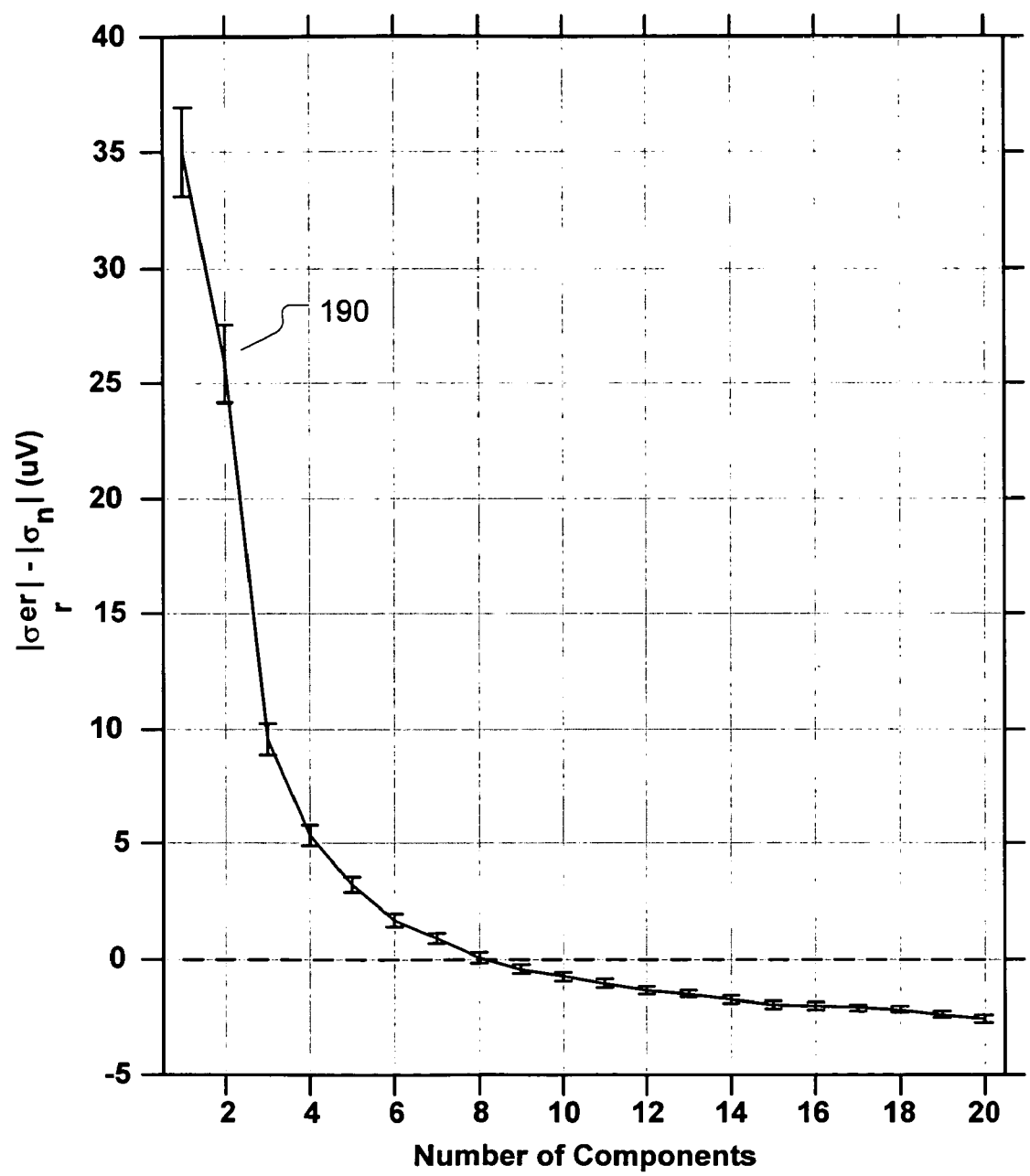
FIG. 11 is a graph illustrating the difference of standard deviations of the errors in the beginning versus in the end of the waveforms in the matrix of evoked neural recording signals as a function of the number of components included according to principles described herein.

FIG. 11 is a graph illustrating the difference of standard deviations of the errors in the beginning versus in the end of the waveforms in M as a function of the number of components included. The error bars (e.g., 190) are approximately 99 percent confidence intervals around the mean estimate of the error. As shown in FIG. 11, the difference becomes zero for eight components. For higher numbers of components, some noise is captured in the measurements. Hence, the error in the beginning portion of the stimulus is less than the standard of deviation.

The results shown in FIGS. 10 and 11 may be used to determine an optimal number of basis functions or components for a given application. For example, seven components capture approximately 98.6 percent of the variance in the data and have a 2 μV mean difference. Thus, seven components are sufficient for many different applications. The examples given herein will use seven components or basis functions. However, it will be recognized that any number of basis functions may be chosen to represent the set of evoked neural recording signals in M.

Figure 12:
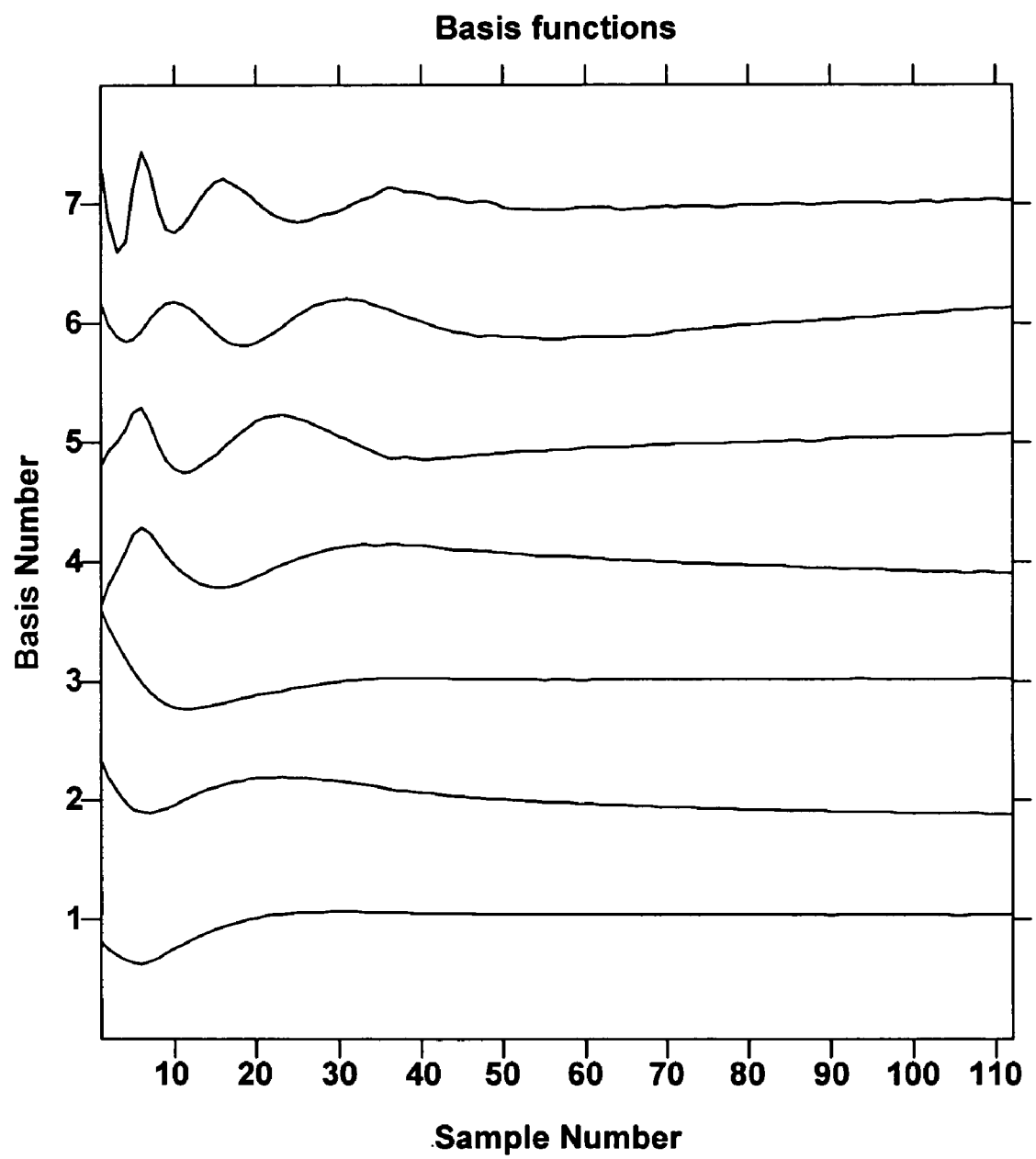
FIG. 12 is a graph showing seven basis functions or components according to principles described herein.

FIG. 12 is a graph showing seven basis functions or components. As shown in FIG. 12, the top basis function (basis function number 7) looks like a neural response signal. The remaining basis functions account for differences in the evoked neural recording signals in M. For purposes of the present example, the seven basis functions or components will be represented by the component matrix $V=[v_1 \ldots v_7]$, where $v_1$ through $v_7$ are vectors representing the seven basis functions. As will be described in more detail below, the component matrix V may be used to denoise an incoming neural recording signal.

Returning to the flow chart of FIG. 9, once the component matrix V has been determined, the next step is to determine relative weights for the basis functions $v_1$ through $v_7$ corresponding to an incoming neural recording signal (step 181). In other words, the amount of each basis function $v_1$ through $v_7$ that is present in the incoming neural recording signal is determined. A computer, digital signal processor (DSP), or any other suitable device or application may be used to determine the relative weights for the basis functions. As will be described in more detail below, the incoming neural recording signal is denoised by multiplying the weights with the basis functions $v_1$ through $v_7$.

For example, assume that the incoming neural recording signal is represented by m. The relative weights for the basis functions $v_1$ through $v_7$ are determined by correlating the incoming neural recording signal m with the basis functions in the component vector V. Hence, the weights are equal to V' m.

As shown in FIG. 9, the weights are then multiplied with the basis functions to denoise the incoming neural recording signal (step 182). Thus, the denoised neural recording signal, $m_{denoised}$, is equal to V V' m. For ease of explanation, $m_{denoised}=T$ m, where T is the denoising matrix equal to V V'. A computer, digital signal processor (DSP), or any other suitable device or application may be used to resynthesize the weights.

Mathematically, the denoising effect of multiplying the weights with the basis functions can be shown by the following equations. Suppose that the incoming neural recording signal is m=s+n, where s represents the evoked neural response signal and/or artifact signal and n represents the uncorrelated noise. Without loss of generality, it can be assumed that n has a zero mean. The denoised waveform is then $m_{denoised}=T$ m=T s+T n=$s_{denoised}$+T n. Therefore, the uncorrelated noise in the denoised waveform is $n_{denoised}=m_{denoised}-s_{denoised}=T$ n.

Conceptually, the denoising effect of multiplying the weights with the basis functions can be illustrated by the following example. Suppose that there is only one basis function and the incoming neural recording only contains noise. When this incoming noise is correlated with the basis function, the resulting weight value is low, indicating that the noise does not correlate with the basis function. When the low weight number is multiplied with the basis function, the resulting signal is characterized by a smaller magnitude than the incoming noise signal.

On the other hand, suppose that the incoming neural recording is noiseless. Therefore, when the incoming neural recording signal is correlated with the single basis function, the resulting weight number is high, indicating that the incoming neural recording signal correlates with the basis function. When the high weight number is multiplied with the basis function, the resulting signal is characterized by a magnitude that is relatively close to the magnitude of the incoming neural recording signal.

Figure 13:
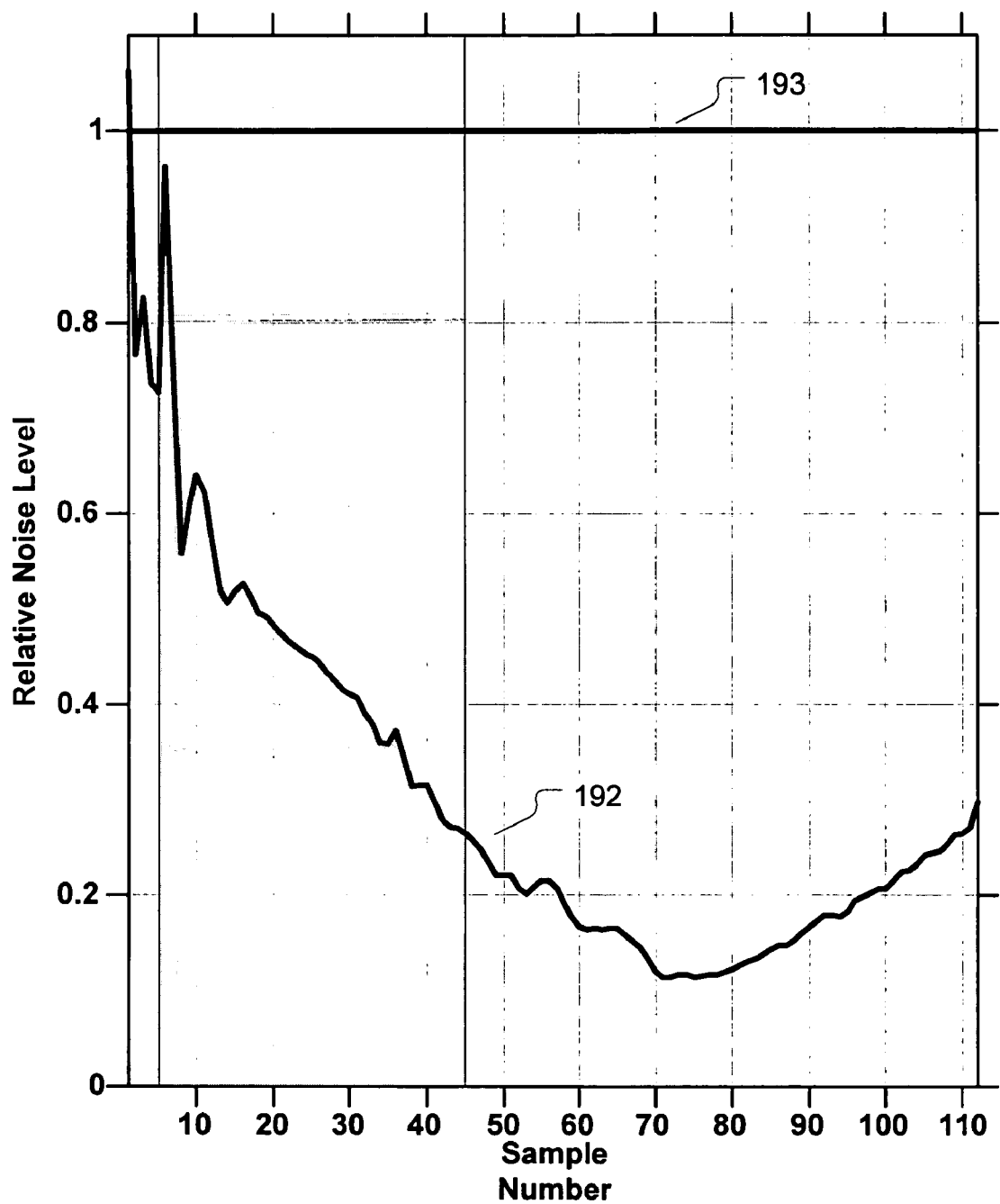
FIG. 13 is a graph showing the amount by which noise is reduced for each point of the waveform representing the incoming neural recording signal according to principles described herein.

The noise can be described by the covariance matrix $CD_n = E[n\, n'] = T\, E[n\, n']\, T' = T\, C_n\, T'$. The diagonal of the matrix $CD_n$ is the variance at any point. Therefore, the square root of the diagonal is equal to the standard deviation at any given point. Assuming that the incoming noise is white, with unity variance, the decrease in the noise standard deviation is shown in FIG. 13. FIG. 13 shows, as a function of sample number, the amount by which noise is reduced for each point of the waveform representing the neural recording. The horizontal line (193) represents the noise level of the incoming neural recording before denoising. The line (192) represents the noise level of the incoming neural recording signal after denoising. The shaded area represents the range of time where most of the response energy is maximal. In this area, as shown in FIG. 13, an average reduction in noise of nearly 50 percent is achieved by the denoising technique described herein.

In some embodiments, greater noise reductions may be achieved by including fewer components. However, the cost of including fewer components may be loss of some energy in the denoised signal.

The denoising method described in connection with FIG. 9 can be shown to be optimal in a sense that any further filtering that preserves the neural response signal entirely does not improve the signal-to-noise ratio. To demonstrate this, consider a filter F for which F's=s, for any s, i.e. this filter will not change the neural response and/or artifact component of the neural recording signal at all. Thus, the filtered response is rdf=F' T s+F' T n. However, if V captures all possible responses s, then by necessity F'V=V. In this case, $CD_{nf} = CD_n$ and the noise matrix is not changed.

Returning to the flow chart of FIG. 8, after the neural recording signal has been denoised (step 213), confidence intervals corresponding to the neural recording signal may be determined (step 214). The confidence intervals take into account the uncertainty in the denoised neural response signal. The confidence intervals may be derived from any combination of a number of contributing factors including, but not limited to, estimates of noise levels, relative noise levels before and after multiplying the weights with the basis functions, and other factors.

As shown in FIG. 8, the method also includes fitting an artifact model to the obtained neural recording signal (step 216). The artifact model describes a typical or model stimulus artifact signal, and, as will be described in more detail below, may be used to determine whether a neural recording signal includes a neural response signal.

As used herein and in the appended claims, unless otherwise specifically denoted, the variable $a_m(t)$ will be used to represent an artifact model. As mentioned, a stimulus artifact signal can be characterized as a sum of two decaying exponentials. Hence, the artifact model may be described by the following equation: $a_m(t) = A_1 \cdot e^{-\alpha \cdot t} + B \cdot e^{-\beta \cdot t}$, where $\alpha$ and $\beta$ are time constants. Since the time constant $\beta$ is large compared to the time scale of interest, the second exponential in this equation can be estimated by a linear trend. Hence, $a_m(t) = A_1 \cdot e^{-\alpha \cdot t} + A_2 \cdot t + A_3$. All of the parameters in this model are linear, except for the coefficient $\alpha$. As will be described in more detail below, the values of the parameters $[\alpha, A_1, A_2, A_3]$ may be adjusted to fit the artifact model to a neural recording signal.

The variable m(t) will be used herein and in the appended claims, unless otherwise specifically denoted, to represent a neural recording signal. Hence, m(t)=a(t)+s(t)+n(t), where a(t) represents the stimulus artifact signal, s(t) represents the neural response signal, and n(t) represents the noise signal. To fit the artifact model $a_m(t)$ to the neural recording signal m(t), the model parameters $[\alpha, A_1, A_2, A_3]$ are determined for which the error between the artifact model and the data within the neural recording signal is minimized. Heuristic optimizations may be applied to limit the artifact model. For example, the parameter $A_1$ may be required to have a positive value. A computer, digital signal processor (DSP), mathematical application, or any other suitable device or application may be used to fit the artifact model $a_m(t)$ to the neural recording signal m(t).

Once the artifact model has been fitted to the neural recording signal (step 216), the fitted artifact model signal is denoised (step 217). The fitted artifact model is denoised to eliminate or reduce distortions or uncertainties in the model due to the noise that is present in the neural recording signal. The fitted artifact model signal may be denoised using principal component analysis, as described above, or by using any other suitable denoising technique.

Figure 14:
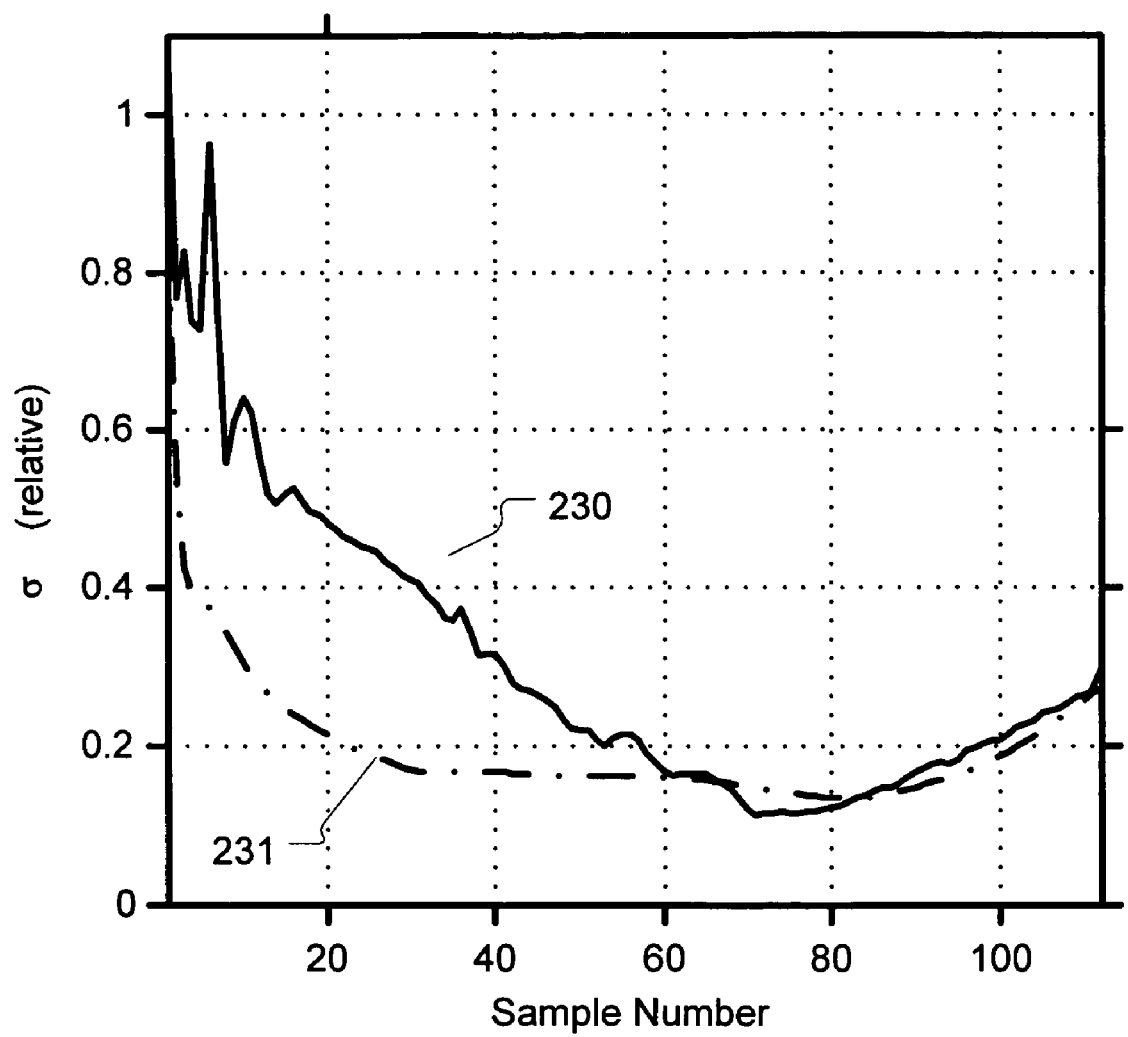
FIG. 14 is a graph illustrating the relative contribution of the noise and the artifact model to the overall uncertainty of the artifact model according to principles described herein.

After the fitted artifact model signal has been denoised (step 217), confidence intervals for the fitted artifact model signal are determined (step 218). These confidence intervals are determined by a number of uncertainties in the artifact parameters given the noise level in the neural recording signal. For example, there may be uncertainty in the stimulus, uncertainty in the model, and uncertainty in the noise. FIG. 14 is a graph illustrating the relative contribution of the noise (230) and the artifact model (231) to the overall uncertainty of the fitted artifact model signal. The results in FIG. 14 and/or additional or alternative factors may be used in determining the confidence intervals for the fitted artifact model signal.

Figure 15A:
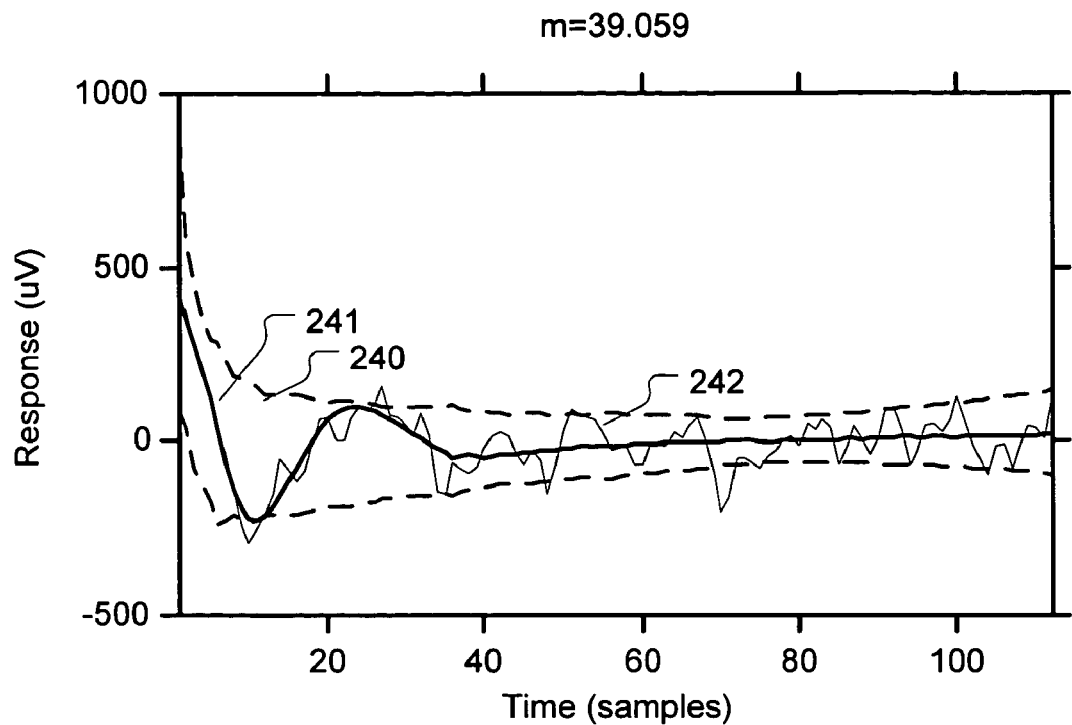
FIGS. 15A and 15B are graphs illustrating net confidence intervals that are used to determine whether a neural recording signal includes a neural response signal according to principles described herein.
Figure 15B:
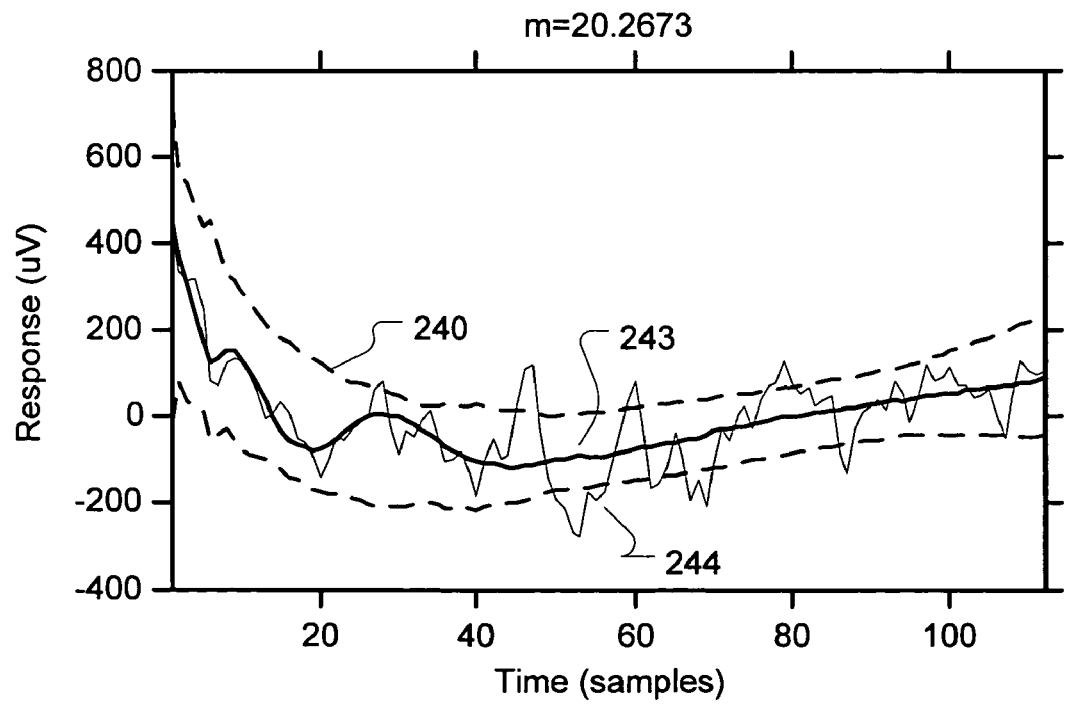

Returning to FIG. 8, once the confidence intervals have been determined for the neural recording signal (step 214) and for the fitted artifact model signal (step 218), net or total confidence intervals are computed by summing the neural recording signal confidence intervals and fitted artifact model signal confidence intervals (step 219). FIGS. 15A and 15B show exemplary net confidence intervals (240). As will be described in more detail below, these net confidence intervals (240) are used to determine whether a neural recording signal includes a neural response signal.

Returning to FIG. 8, after the net confidence intervals have been computed (step 219), a strength-of-response (SOR) metric corresponding to the observed neural recording signal is computed (step 220). The SOR metric describes the distance of the fitted artifact model signal to the observed neural recording signal relative to the net confidence intervals (240). A neural recording signal may be identified as including a neural response signal if the SOR metric exceeds a pre-determined threshold.

The SOR metric may be any metric that describes the distance of the fitted artifact model signal to the observed neural recording signal relative to the net confidence intervals (240). A number of different SOR metrics may be used. One exemplary SOR metric is $$SOR = \sqrt[6]{\frac{1}{35} \sum_{t \in [22,57]} \left(\frac{(\overline{m}(t) - \overline{a}_m(t))}{c(t)}\right)^6},$$

where c(t) is the net confidence interval size. This equation may be modified as best serves a particular application.

The size of the SOR metric is then evaluated (step 221) to determine whether the neural recording signal includes a neural response signal or whether the neural recording signal only includes noise and artifact signals. The SOR metric evaluation may be performed automatically with a computer, DSP, mathematical application, or any other suitable device or application. If the SOR metric exceeds a pre-determined threshold, the neural recording signal is identified as including a neural response signal (222). Conversely, if the SOR metric is below the pre-determined threshold, the neural recording signal is identified as not including a neural response signal (step 224).

Additionally or alternatively, further neural recording signals may be obtained and averaged (step 223) if the SOR metric is too close to the threshold to accurately identify as corresponding to a neural recording signal that includes a neural response signal or not. A new SOR metric may be computed and evaluated for these additional neural recording signals.

An example of determining whether a neural recording signal includes a neural response signal by evaluating the SOR metric will be described in connection with FIGS. 15A and 15B. FIG. 15A shows a first exemplary neural recording signal (242) and a corresponding denoised neural recording signal (241) that has been fitted by the artifact model. As shown in FIG. 15A, the denoised recording signal (241) is relatively close to the confidence interval (240) and may therefore be difficult to visually identify as including a neural response signal. However, suppose that the pre-determined SOR threshold is m=35. Using the SOR metric equation shown above, the SOR metric for the denoised recording signal (241) is equal to m=39.059, well above the threshold value of 35. Therefore, the neural recording signal (242) may be identified as including a neural response signal.

FIG. 15B shows a second exemplary neural recording signal (244) and its corresponding denoised neural recording signal (243) that has been fitted by the artifact model. The SOR metric for this neural recording signal (244) is equal to m=20.2673, well below the threshold value of 35. Therefore, the neural recording signal (244) may be identified as not including a neural response signal.

Figure 16:
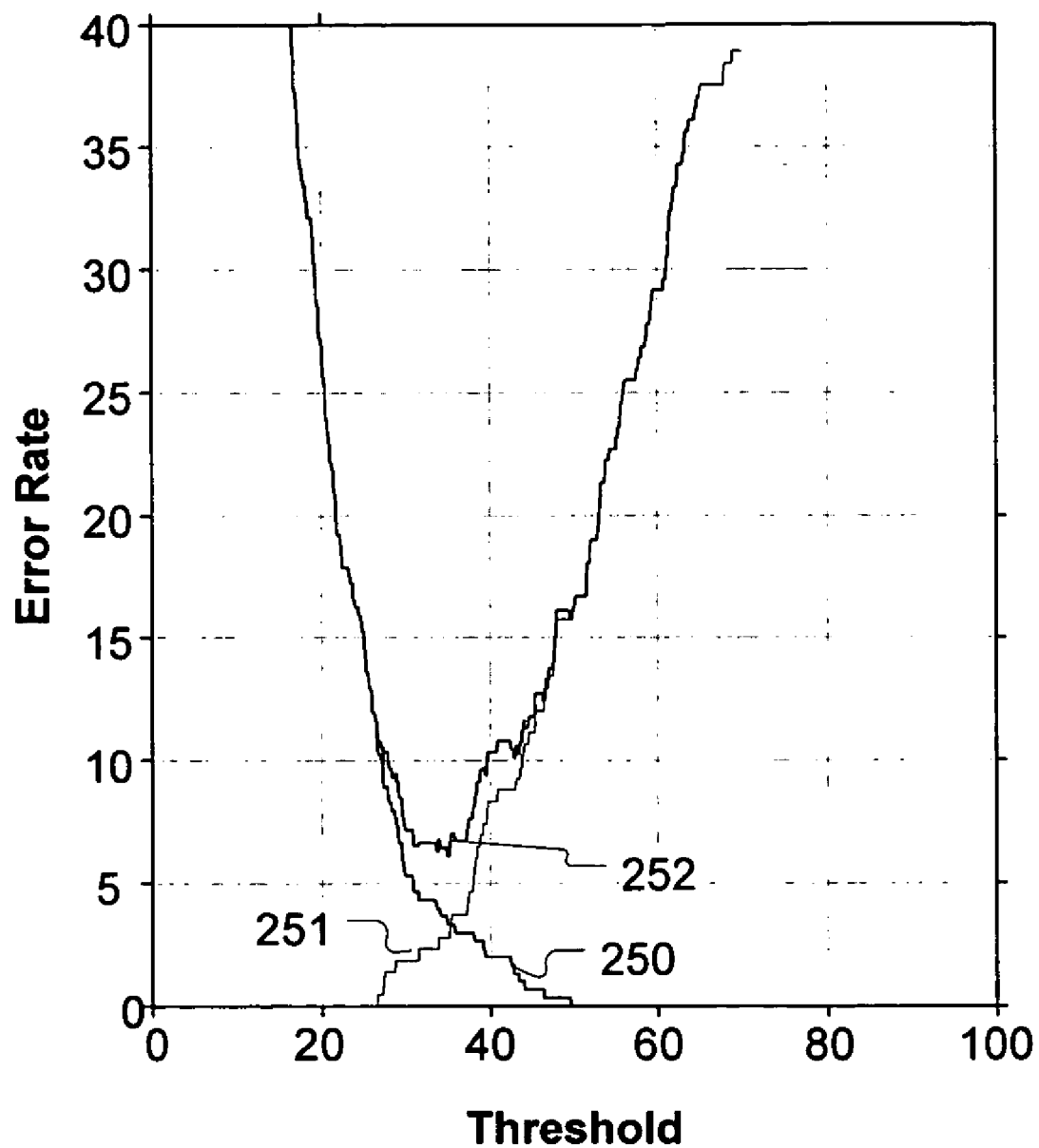
FIG. 16 is a graph that shows error rates of the automatic neural response identification method when compared to visual identification of neural response signals by expert medical practitioners for a number of different threshold values according to principles described herein.

An optimal threshold value may be determined using a number of different techniques. In some embodiments, the optimal threshold value is determined by comparing the results of the automatic neural response identification method of FIG. 8 to the results of visual identification of the same neural response signals by expert medical practitioners. For example, FIG. 16 is a graph that shows error rates of the automatic neural response identification method when compared to visual identification of neural response signals by expert medical practitioners for a number of different threshold values. Curve (250) shows the percentage of "false positives" (i.e., the percentage of neural recording signals falsely identified as including a neural response signal) per threshold value, curve (251) shows the percentage of "false negatives" (i.e., the percentage of neural recording signals falsely identified as not including a neural response signal) per threshold value, and curve (252) shows the net error rate per threshold value. The optimal threshold value is determined by choosing the threshold value that corresponds to the minimum value of the net error rate curve (252). Hence, the optimal threshold value for the curves shown in FIG. 16 is approximately equal to 35.

The method illustrated in FIG. 8 of automatically identifying a neural recording signal as including a neural response signal may be performed by an application, processor-readable instructions, or the like that may be stored in a processor readable medium. The processor readable medium may be a hard drive, optical disc, or any other storage device medium.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of automatically identifying whether a neural recording signal includes a neural response signal, said method comprising:
   providing an artifact model that describes a model stimulus artifact signal that is correlated with a stimulus used to evoke said neural recording signal, said artifact model being represented by a plurality of model parameters;
   fitting, by a computer, said artifact model to a neural recording signal to produce a fitted artifact model signal, said fitting comprising determining values for said model parameters that result in a minimized error between the artifact model and said neural recording signal;
   determining, by the computer, a strength-of-response (SOR) metric that describes a distance of said neural recording signal from said fitted artifact model signal; and
   identifying, by the computer, said neural recording signal as including a neural response signal if said strength-of-response metric is above a pre-determined threshold.

2. The method of claim 1, further comprising identifying said neural recording signal as including only noise and/or stimulus artifact if said strength-of-response metric is below said pre-determined threshold.

3. The method of claim 1, further comprising averaging additional neural recording signals if said strength-of-response metric is within a pre-determined distance from said pre-determined threshold.

4. The method of claim 1, further comprising conditioning said neural response signal and estimating an amount of noise in said neural recording signal prior to fitting said artifact model to said neural recording signal.

5. The method of claim 1, further comprising denoising said neural recording signal and said fitted artifact model signal prior to determining said strength-of-response metric.

6. The method of claim 5, wherein said step of denoising said neural recording signal and said fitted artifact model signal comprises using principal component analysis.

7. The method of claim 1, further comprising:
   determining a net confidence interval corresponding to said fitted artifact model signal and said neural recording signal; and
   using said net confidence interval to determine the strength-of-response metric.

8. The method of claim 1, wherein said strength-of-response metric is determined by evaluating $$SOR = \sqrt[6]{\frac{1}{35} \sum_{t \in [22,57]} \left( \frac{(\overline{m}(t) - \overline{a}_m(t))}{c(t)} \right)^6},$$

where $\overline{m}(t)$ corresponds to said neural recording signal, $\overline{a}_m(t)$ corresponds to said fitted artifact model signal, and $c(t)$ represents a size of a net confidence interval corresponding to said neural recording signal and said fitted artifact model signal.

9. The method of claim 1, wherein the artifact model is represented by $a_m(t)$, wherein $a_m(t)$ is equal to $A_1 * e^{-\alpha t} + A_2 * t + A_3$, and wherein $\alpha$, $A_1$, $A_2$, and $A_3$ comprise the plurality of model parameters.

10. A method of automatically identifying whether a neural recording signal includes a neural response signal, said method comprising:
   fitting, by a computer, an artifact model to a neural recording signal to produce a fitted artifact model signal;
   determining, by the computer, a strength-of-response (SOR) metric that describes a distance of said neural recording signal from said fitted artifact model signal; and
   identifying, by the computer, said neural recording signal as including a neural response signal if said strength-of-response metric is above a pre-determined threshold;
   wherein said strength-of-response metric is determined by evaluating $$SOR = \sqrt[6]{\frac{1}{35} \sum_{t \in [22,57]} \left( \frac{(\overline{m}(t) - \overline{a}_m(t))}{c(t)} \right)^6},$$

where $\overline{m}(t)$ corresponds to said neural recording signal, $\overline{a}_m(t)$ corresponds to said fitted artifact model signal, and $c(t)$ represents a size of a net confidence interval corresponding to said neural recording signal and said fitted artifact model signal.

11. A system for automatically identifying whether a neural recording signal includes a neural response signal, said system comprising one or more devices configured to:
   provide an artifact model that describes a model stimulus artifact signal that is correlated with a stimulus used to evoke said neural recording signal, said artifact model being represented by a plurality of model parameters;
   fit said artifact model to a neural recording signal to produce a fitted artifact model signal by determining values for said model parameters that result in a minimized error between said artifact model and said neural recording signal;
   determine a strength-of-response (SOR) metric that describes a distance of said neural recording signal from said fitted artifact model signal; and
   automatically identify said neural recording signal as including a neural response signal if said strength-of-response metric is above a pre-determined threshold.

12. The system of claim 11, wherein said one or more devices comprises at least one or more of a computer, digital signal processor, and software application.

13. The system of claim 11, wherein said one or more devices are further configured to identify said neural recording signal as including only noise and/or stimulus artifact if said strength-of-response metric is below said pre-determined threshold.

14. The system of claim 11, wherein said one or more devices are further configured to average additional neural recording signals if said strength-of-response metric is within a pre-determined distance from said pre-determined threshold.

15. The system of claim 11, wherein said one or more devices are further configured to:
   determine a net confidence interval corresponding to said fitted artifact model signal and said neural recording signal; and
   use said net confidence interval to determine the strength-of-response metric.

16. A system for automatically identifying whether a neural recording signal includes a neural response signal, said system comprising:
   means for fitting an artifact model to a neural recording signal to produce a fitted artifact model signal;
   means for determining a strength-of-response (SOR) metric that describes a distance of said neural recording signal from said fitted artifact model signal; and
   means for identifying said neural recording signal as including a neural response signal if said strength-of-response metric is above a pre-determined threshold;
   wherein said strength-of-response metric is determined by evaluating $$SOR = \sqrt[6]{\frac{1}{35} \sum_{t \in [22,57]} \left( \frac{(\overline{m}(t) - \overline{a}_m(t))}{c(t)} \right)^6},$$

where $\overline{m}(t)$ corresponds to said neural recording signal, $\overline{a}_m(t)$ corresponds to said fitted artifact model signal, and $c(t)$ represents a size of a net confidence interval corresponding to said neural recording signal and said fitted artifact model signal.

17. The system of claim 16, further comprising means for conditioning said neural response signal and means for estimating an amount of noise in said neural recording signal prior to fitting said artifact model to said neural recording signal.

18. The system of claim 16, further comprising means for denoising said neural recording signal and said fitted artifact model signal prior to determining said strength-of-response metric.

19. The system of claim 16, further comprising means for identifying said neural recording signal as including only noise and/or stimulus artifact if said strength-of-response metric is below said pre-determined threshold.

20. The system of claim 16, further comprising means for averaging additional neural recording signals if said strength-of-response metric is within a pre-determined distance from said pre-determined threshold.

* * * * *